(12) United States Patent
Lec

(10) Patent No.: US 7,975,547 B2
(45) Date of Patent: Jul. 12, 2011

(54) METHOD AND APPARATUS FOR INTERFACIAL SENSING

(75) Inventor: Ryszard M Lec, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 593 days.

(21) Appl. No.: 11/719,895

(22) PCT Filed: Nov. 23, 2005

(86) PCT No.: PCT/US2005/042728
§ 371 (c)(1),
(2), (4) Date: Feb. 21, 2008

(87) PCT Pub. No.: WO2007/040566
PCT Pub. Date: Apr. 12, 2007

(65) Prior Publication Data
US 2009/0165559 A1    Jul. 2, 2009

Related U.S. Application Data

(60) Provisional application No. 60/630,380, filed on Nov. 23, 2004.

(51) Int. Cl.
*G01N 29/36* (2006.01)
*G01N 29/44* (2006.01)

(52) U.S. Cl. .............. 73/579; 73/597; 73/602

(58) Field of Classification Search ............ 73/579, 73/599, 602, 597; 702/106, 191, 56, 183, 702/185; 381/71.1, 71.2, 73.1; 436/527, 436/518

See application file for complete search history.

(56) References Cited

U.S. PATENT DOCUMENTS

| | | | |
|---|---|---|---|
| 4,361,026 A * | 11/1982 | Muller et al. | 73/24.01 |
| 4,735,906 A * | 4/1988 | Bastiaans | 436/527 |
| 5,001,053 A * | 3/1991 | Takahashi et al. | 435/7.1 |
| 5,784,300 A | 7/1998 | Neumeier et al. | |
| 6,210,331 B1 | 4/2001 | Raz | |
| 6,313,564 B1 * | 11/2001 | Kataoka et al. | 310/316.01 |
| 6,392,745 B1 * | 5/2002 | Mavliev et al. | 356/37 |
| 6,442,319 B1 | 8/2002 | Dietz et al. | |
| 6,529,809 B1 | 3/2003 | Breed et al. | |
| 6,631,333 B1 | 10/2003 | Lewis et al. | |
| 6,633,821 B2 | 10/2003 | Jackson et al. | |
| 6,642,061 B2 * | 11/2003 | Ellson et al. | 436/180 |
| 6,869,551 B2 * | 3/2005 | Lee et al. | 264/9 |
| 7,266,995 B2 * | 9/2007 | Skogo et al. | 73/64.52 |
| 2002/0176144 A1 | 11/2002 | Bergano et al. | |
| 2003/0204347 A1 | 10/2003 | Smith | |
| 2004/0177680 A1 * | 9/2004 | Skogo et al. | 73/64.51 |

* cited by examiner

Primary Examiner — Jacques M Saint Surin
(74) Attorney, Agent, or Firm — Woodcock Washburn, LLP

(57) ABSTRACT

A sensor is disclosed for analyzing information, such as interfacial interactions, found in various systems. A sensor is located proximate to an interface that is to be studied. The sensor is actuated in order to produce acoustical signals. The frequency of oscillation of the sensor is varied in order to enable the sensor to produce acoustical signals at different harmonics. The different acoustical signals are used to analyze the system at various distances from the surface of the sensor.

50 Claims, 33 Drawing Sheets

SURFACE OF A TSM SENSOR

SURFACE OF A TSM SENSOR

SURFACE OF THE TSM SENSOR 6 mm

SURFACE OF TSM SENSOR

SURFACE OF TSM SENSOR

SURFACE OF TSM SENSOR

METHOD AND APPARATUS FOR INTERFACIAL SENSING

CROSS-REFERENCE TO RELATED APPLICATIONS

This application is the National Stage of International Application No. PCT/US2005/042728 filed Nov. 23, 2005, which claims the benefit of U.S. Provisional Application No. 60/630,380, filed Nov. 23, 2004, the disclosure of which is incorporated herein by reference in its entirety.

BACKGROUND OF THE INVENTION

1. Field of the Invention

The invention relates to the field of sensors. In particular the invention relates to sensors adapted for sensing in the area of interfaces involving biological, medical, chemical and physical processes.

2. Description of the Related Technology

Most physical, chemical and biological processes are surface driven. Biological processes and their outcomes are determined by the properties of the surfaces and interfacial areas of biological entities such as bones, membranes, cells, proteins, as well as their interaction with man-made materials such as polymers, metals (titanium, other), etc. Chemical processes involve formation of coatings such as suspensions, colloids, paints, corrosion protective layers, or catalytic processes, etc. Physical processes relate to gaseous, liquid and solid phase condensation, fabrication of thin films of various materials such as polymers, metals, metal oxides, crystals and polycrystals, (silicon, zinc oxide, etc,) or material modification via such processes as implantation, doping, etc. Typically, such interfacial areas exhibit nonuniform properties and consist of many different surfaces or sub-interfaces that form a multi-layered structure and/or different regions in the interfacial area.

FIGS. 1a-1b show a titanium implant 1 and bone 2 interface at various different levels of depth and layer thickness. FIG. 1a shows the interaction between the bone 2, the titanium implant 1 and bio-fluid 4 at the depth of roughly 1 μm from the bone/titanium interface. FIG. 1b shows the interaction between a titanium layer 1a and a titanium oxide layer 1b of the titanium implant 1 and the biofluid 4 at a depth of 1 nm from the bone/titanium interface. The interactions at different depths from the interface provide important information about what processes are going on between the titanium implant and the body. Similarly, in interfacial areas involving chemicals such as paints, one can distinguish several regions exhibiting different properties. In the case of physical processes, a typical example of an interfacial area having different layers or regions is a multi-layer structure of silicon material.

Therefore, in order to understand and monitor such processes as biocompatibility, drug interaction, cell-substrate interaction, tissue engineering, nanotechnology, absorption, and successfully design biological, medical, chemical and physical devices that are capable of addressing these needs, it is helpful to interrogate these surfaces and interfacial areas at different depths from the interface of interest, as shown in FIG. 2. Ideally, the interrogating method should be capable of providing information at different depths from an interface, or, in other words, slice interfacial areas at different depths. As a result of such an interrogation process, a map of the properties of individual layers or regions forming the interfacial area will be created. It is also advantageous to obtain information on the whole interfacial area as a result of the interrogation procedure.

Sensing mechanisms employed today do not typically seek to obtain information at different distances from the interface. A standard sensing mechanism will typically only try to detect the presence of certain objects and items using a single frequency (wavelength) and thus will obtain only a single information input for a specific portion of the interfacial area. Most sensors do not have the capability to interrogate the interfacial area at different distances from an interface or at different spatial resolutions.

Existing methods provide the means of interrogating in the area of an interface at only a single depth. Existing methods are based on optical, electrical and acoustical means, or sensing mechanisms. The optical methods utilize optical evanescent waves of a given frequency or wavelength. The typical frequency range of operation includes the visible range of optical waves which provide a depth of penetration on the order of 0.5-0.8 micrometers. An example of this single-depth optical technique for providing information about an interfacial area is surface plasmon resonance (SPR). Though SPR is used widely, it provides only limited information on interfacial processes. Electrical methods utilize a system of electrodes placed on the surface of the interrogating element, which subsequently is exposed to a detectable object. Here, the depth of penetration is on the order of tens of microns with very limited spatial resolution. Acoustic techniques utilize a single-depth. In all of these cases the depth of penetration is not a factor to be considered. Moreover, these processes do not provide resolutions in the nanometer range.

The techniques mentioned above do not have the ability to gather as much information as would be helpful to understand some complex processes, such as biocompatibility, drug interaction, cell-substrate interaction, tissue engineering, nanotechnology, absorption, and interactions with semiconductor devices (microchips). In order to better understand these and other systems involving non-uniform interfacial areas it is necessary to interrogate the interfacial area at different depths to obtain a more complete understanding of the processes that are taking place in the interfacial area.

Therefore, there exists a need for providing a more flexible and effective method and apparatus for interpreting and interrogating the interactions between different materials on a microscopic and nanoscopic scale.

SUMMARY OF THE INVENTION

Accordingly, it is an object of certain embodiments of the invention to provide a more flexible and effective method and apparatus for interrogating and interpreting interfacial processes and the interactions between different materials on a microscopic and nanoscopic scale.

In a first aspect of the invention a sensor is actuated by an actuator. The actuator is enabled for exciting the sensor to multiple sensing modalities (operating conditions) in order to provide information at different distances, or penetration depths, from the sensor. In particular, the sensor can be excited at different operating frequencies, which enable the sensor to interrogate the interface at different depths.

In a second aspect of the invention, a method for interfacial sensing is disclosed. The method involves providing a sensor, exciting the sensor at a its first operating condition, measuring a response of the sensor, changing the excitation signal of the sensor to a next operating condition, and measuring the sensor response at this operating condition.

In particular, the method involves providing a sensor, exciting the sensor at a first frequency, measuring a resonance feature of the sensor, changing the excitation frequency of the sensor to at least one additional frequency, and measuring a resonance feature of the sensor at the at least one additional frequency.

In a third aspect of the invention, a method for sensing is disclosed. The method involves selecting an interrogation distance from a surface of a sensor, exciting the sensor at its operating conditions that interrogates at the selected interrogation distance from the surface of the sensor, and measuring a response of said sensor. In particular, the method involves selecting an interrogation distance from a surface of a sensor, exciting the sensor at a frequency that interrogates at the selected interrogation distance from the surface of the sensor, and measuring a resonance feature of said sensor.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

In most biological applications, and in many biochemical applications, information regarding ongoing surface-mediated, or interfacial processes is provided by analysis of the ongoing mechanical processes. For example, the change in mechanical properties of the cells attaching to a man-made material provide information on the biocompatibility of the man-made material, or, for example, the mechanical properties of immobilized antibodies (Ab) on the surface of a functionalized sensor provide information on the effectiveness and quality of the Ab attachment process. A method and apparatus according to an exemplary embodiment of the instant invention can directly measure the mechanical or viscoelastic properties of interfacial areas. According to this exemplary embodiment, a Multiresonant Acoustic Interfacial Analyzer (MAIA) interrogates an interface with an acoustic wave at multiple resonant conditions.

Since the length scale desired in order to interrogate the different depths of various biological and biochemical objects and processes is on the order of nanometers-micrometers, it is important that the method of interrogation provides the same scale of analysis (i.e., resolution) as that of the interfacial area. The method and apparatus for the multi-resonant acoustic interrogation technique is capable of both simultaneous and/or sequential analysis of interfacial areas at different depths with high spatial (nm) and temporal (msec) resolutions.

The MAIA comprises a sensor, which may be one of any number of sensor-types so long as it is possible to vary the oscillation conditions (frequency, amplitude, phase, etc) of the sensor. The MAIA sensor may be manipulated via electrical means, optical means, magnetic means, electromagnetic means, or thermal means. In an exemplary embodiment of the invention, the MAIA sensor is a type of thickness shear mode sensor (TSM). Alternatively, the sensor may be a sensor that detects torsional motion, radial motion, shear motion, or a combination of different types of motion. The MAIA sensor can utilize other sensing modalities like optical, electromagnetic, magnetic, electric, etc. The response of the MAIA sensor depends on interfacial processes, such as mass accumulation or changes in mechanical properties (elasticity, viscosity, density, and thickness) of adjacent material. These mechanical properties will create changes in the MAIA response features or parameters, such as resonance parameters, for example. Response parameters that can be used include: amplitude, voltage, current, impedance, admittance, transimpedance, scattering parameters, transmission parameters, phase, Q-factor, frequency, and their combinations. These parameters can be determined at the resonance, anti-resonance, harmonic and inharmonic frequencies.

Figure 2:
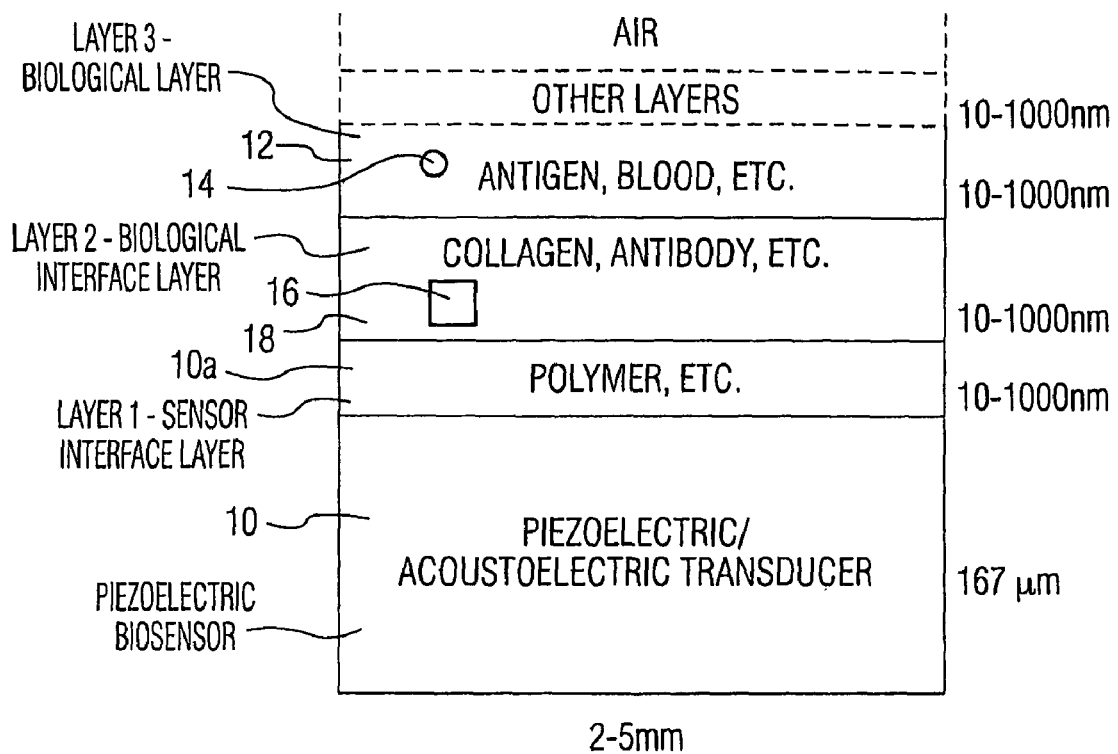
FIG. 2 shows a diagram of various regions or layers of an interfacial area.

FIG. 2 shows an exemplary MAIA comprising a piezoelectric sensor 10 used in a system comprising blood 12, antigens 14, collagen 16, and antibodies 18. The piezoelectric sensor has a polymer surface layer 10a. FIG. 2 shows the various layers or regions that can be interrogated by the exemplary MAIA sensor 10 via adjustment of the sensor's oscillation frequency. With the system in FIG. 2 it is possible to gather information about the interaction between the antigens, located in layer 3, and antibodies located in layer 2. In a standard sensor there would generally be no ability to interpret the differences between these layers in the systems.

Figure 3:
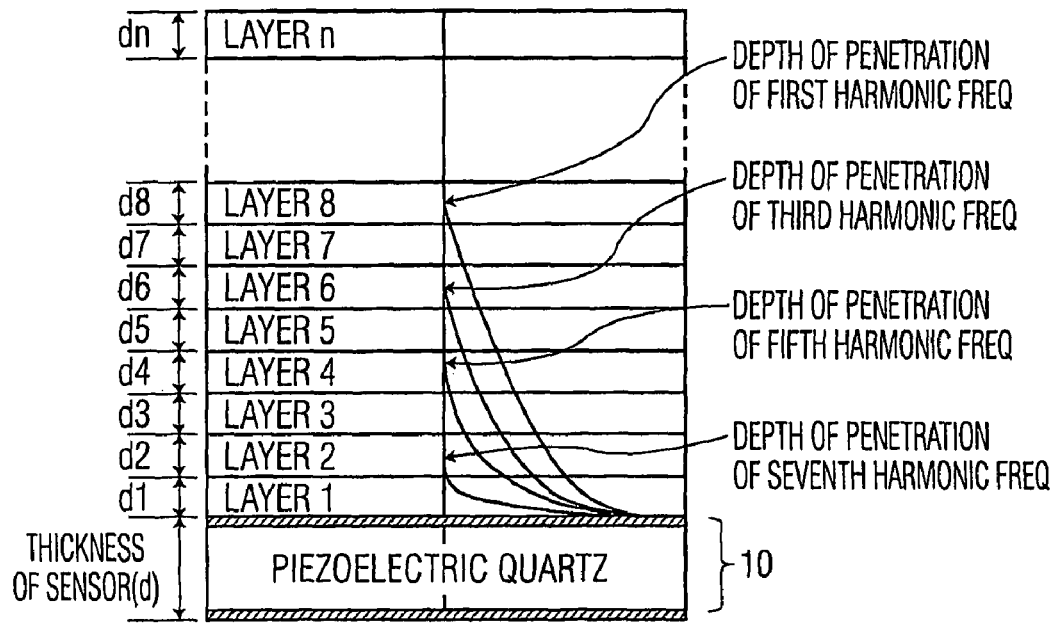
FIG. 3 shows a diagram of the depth of penetration of a multi-resonant interrogation method according to an exemplary embodiment of the invention at various harmonic frequencies.

FIG. 3 shows that the depth of penetration that can be interrogated varies based upon the harmonic frequency of the sensor 10. This enables one to gather information regarding a plurality of possible interfacial interactions that occur in the system and does not limit one to simply monitoring the system at one depth, as is the case with most prior art sensors.

Figure 4:
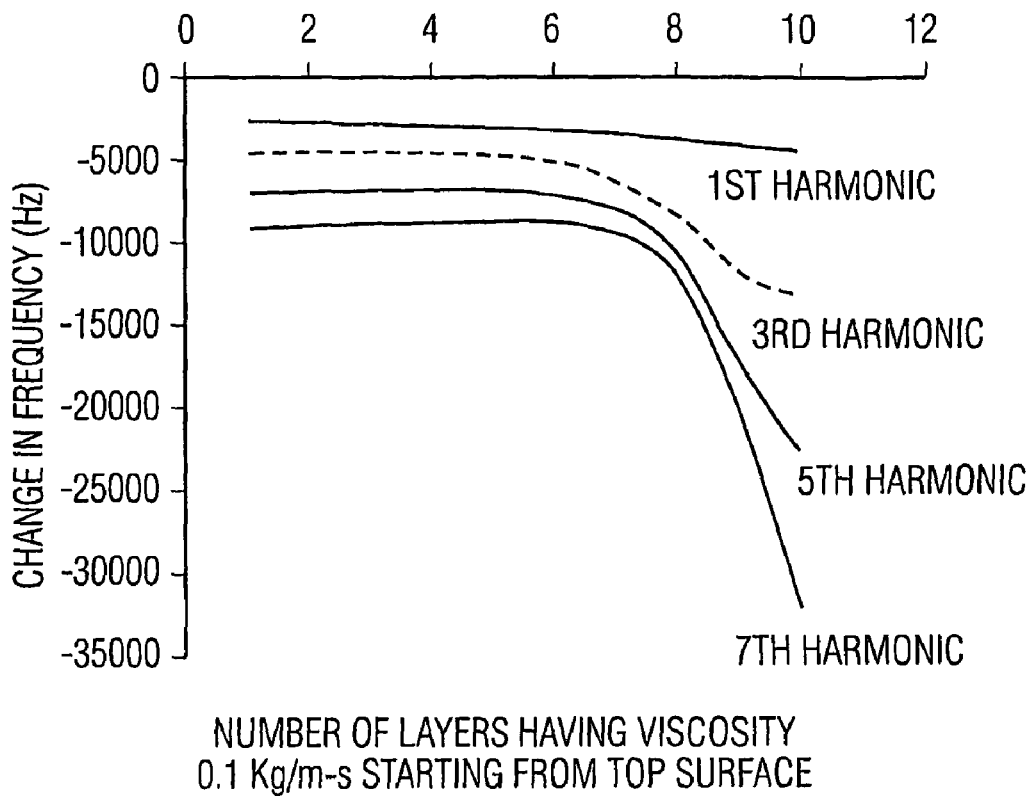
FIG. 4 shows a graph showing a change in frequency response for a change in viscosity of a load in the direction from the top surface towards the sensor surface.

According to an exemplary embodiment, an MAIA may be used to measure the amount of sedimentation in a system. FIG. 4 shows the response of a 10 MHz MAIA sensor to sedimentation at various harmonics. It can be seen from the graph that as the number of layers of sedimentation increase the various harmonics have a change in frequency. This permits a detailed analysis of the sedimentation process in the system.

Figure 5A:
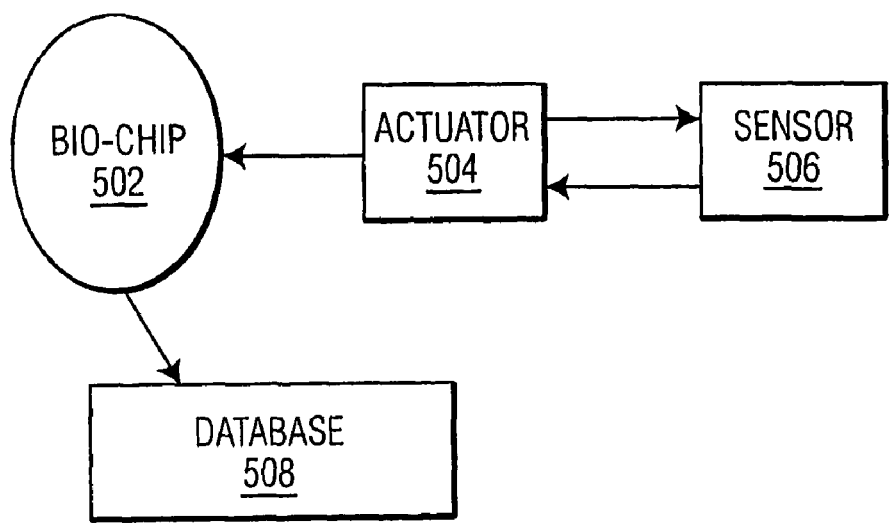
FIG. 5a shows a flow chart showing a sensor system according to an exemplary embodiment of the invention.

FIG. 5A shows an overview of an exemplary system used for interrogating interfacial interactions. The system comprises chip 500, with: signal conditioning and processing (SCP) 502, actuator 504, sensor 506, and database 508. In the typical operation of the system, sensor 506 is oscillated via the actuator 504. Actuator 504 can use various means to oscillate sensor 506, such as optical means, magnetic means, electromagnetic means, and thermal means. Chip 500 can be a specialized bio-chip, for example, that is designed to function within a living organism, such as humans. The sensor shown in FIG. 2 is made of piezoelectric crystal. Various measurements, such as frequency, amplitude, phase, voltage, and current, can be taken based on the resonance features, which relate to the interaction of the sensor and the various layers interrogated. These measurements can be taken and interpreted at SCP 502. SCP 502 is used to analyze the data and provide information regarding the received measurements. For instance, sensor 506 could be used to detect dangerous microbes and SCP 502 could make the determination that a dangerous microbe is present after interpreting the data. Chip 500 could then transmit a signal in order to indicate that a dangerous microbe is present.

In FIG. 5A an overview of an exemplary apparatus and method for sensing is depicted. In the method the depth of penetration (i.e. the distance from the sensor) of a signal (wave) interrogating the interface is useful for analysis of the interfacial area. Specifically, the depth of penetration is used as a variable for collecting information about the interfacial processes, and is included in the development process of the interrogating interface. The method utilizes a multi-depth interrogation of the interfacial area in order to obtain spatial information on the properties of that interfacial area.

A technique for implementing interfacial sensing involves providing a sensor, and varying the sensor's operating conditions in order to provide multi-depth interrogation. The sensor operation can be based on acoustic, optical, electromagnetic, magnetic, electric, thermal and nuclear sensing mechanisms.

In an exemplary embodiment, sensor 506 can be an acoustic sensor. As an acoustic sensor, sensor 506 is excited by actuator 504. In particular, sensor 506 is oscillated by actuator 504. Actuator 504 is enabled for oscillating sensor 506 at different frequencies of oscillation. Under excitation by actuator 504, sensor 506 generates an acoustic wave, which can be used to interrogate different regions of the interfacial area. In particular, the interrogating wave could be shear, torsional, compressional, or a combination of two or more of these.

Computational software for modeling the sensor and predicting its response to the given interfacial structure or process can be used. This modeling uses a system of Maxwell, Faraday, Newton, and Fourier equations describing interrogating signals, and the constitutive equations that describe the properties of the surfaces and interfaces. These equations are coupled by the boundary conditions that specify the types of interactions that occur between given interfaces. This system of equations is solved for a given parameter, which is measured by the sensor. These parameters may include, for example, frequency, amplitude, voltage, current, impedance, admittance, scattering and transmission parameters or their combinations.

The multi-depth interrogation of the interfacial area gives unique sensor responses obtained at different penetration depths. These unique responses produce signatures that in a unique way characterize a specific interfacial process. The properties of the signatures, in turn, enhance important sensor operational/technical features such as selectivity, sensitivity, immunity to ambient conditions, etc. As a result, multi-depth interrogation allows creation of a library of signatures that correspond to specific interfacial processes, hence expanding the use of the method as well as improving its reliability.

The measured resonance features of sensor 506 can include frequency, amplitude, voltage, current, phase, impedance, admittance, transimpedance, scattering parameters, transmission parameters and their combinations. In particular, these listed above parameters can be determined at the resonance antiresonance, harmonic and inharmonic frequencies.

Chip 500 can analyze the information received itself at database 510, or alternatively send the information received to a database located at another location, such as via a wireless transmitter. Also, the sensor reading need not be routed via actuator 504 to SCP 502, but instead could be routed directly to SCP 502. Database 510 can be used in order to develop signatures for different types of signals received. By compiling and analyzing the information received, it will be possible to eventually match received data with its corresponding signature in order to produce more accurate results. Simple to very complex pattern recognition techniques might be implemented depending on the application. Such techniques include K-nearest neighbor (KNN), Canonical Discriminate Analysis (CDA), Soft Independent Modeling of Class Analogy (SIMCA), probabilistic neural network (PNN), artificial neural network (ANN), support vector machine (SVM), Fisher Linear Discriminate (FLD) and others.

In certain exemplary embodiments of the invention a plurality of sensors 506 and/or a plurality of actuators 504 may be provided.

Figure 5B:
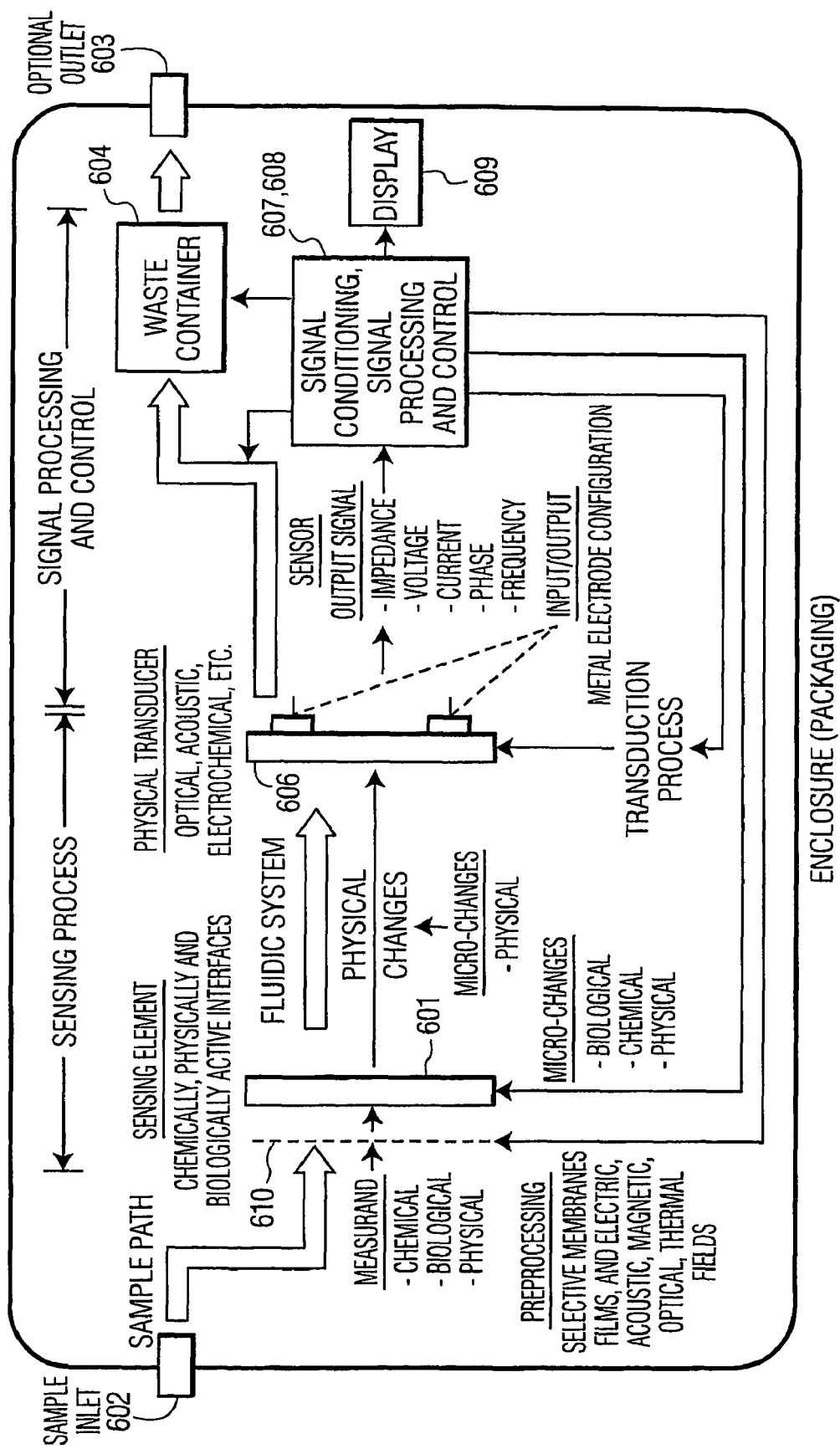
FIG. 5b shows a functional diagram of a sensor system according to an exemplary embodiment of the invention.

FIG. 5B shows another exemplary sensing system 600 according to an embodiment of the present invention. Sample material 601 may be introduced to the sensor system 600 through an inlet 602. After the interrogation process, sample material 601 may be stored in a waste container 604 or may be expelled through an outlet 603.

The exemplary sensing system 600 comprises sensor 606, which may be, for example an acoustic transducer, such as a TSM piezoelectric transducer. An actuator 607 is enabled to excite the sensor 606 at pre-selected or at variable operating parameters. These operating parameters may include frequency, amplitude, phase, impedance, voltage, and current. A signal processor 608 captures the response of the sensor 606. This response is dependant on the operating parameters, as well as the interfacial process occurring at the sensor surface. For example, the sensor 606 may be excited at a lower amplitude, which interrogates the sample non-destructively (i.e., the structure of the sample measurant remains intact). At low amplitudes, the select response parameters do not change between different amplitudes. Conversely, at higher amplitudes, the sample is interrogated destructively (i.e., constituent components of the measurant are released), and the select response parameters shift significantly. The captured response includes one or more response features such as: frequency, amplitude, Q-factor, and phase. Optionally, the signal processor 608 and the actuator 607 may be combined as a single unit. Optionally, the response may be output on a display 609 and be presented as a viewable waveform.

FIG. 5b also shows an optional preprocessor 610. The pre-processor 610 may provide selectivity of material exposed to the sensor or to a reactant. The pre-processor may also enhance sensitivity of the sample material 601. The pre-processor may comprise one or more of: a selective membrane, films, electrical, magnetic, acoustic, and optical fields, and a thermal gradient. These pre-processors will selectively pass or restrict specific materials or change their properties to achieve desirable boundary conditions.

Provided below are various examples that utilize sensor systems according to various embodiments of the invention for interrogating the interfacial interactions of systems.

Example 1

Collagen and Albumin Thin Film

In an exemplary embodiment of the invention, an MAIA sensor is used to study the formation of biological thin films of collagen and albumin. The MAIA sensor, in this example, is constructed out of a piezoelectric material.

Biological thin films play a significant role in using biosensors where they provide selective interfaces for detection of various biochemical analytes. In this example a quartz crystal has been fabricated to function as an MAIA to study the thin film formation processes of collagen and albumin.

Figure 6:
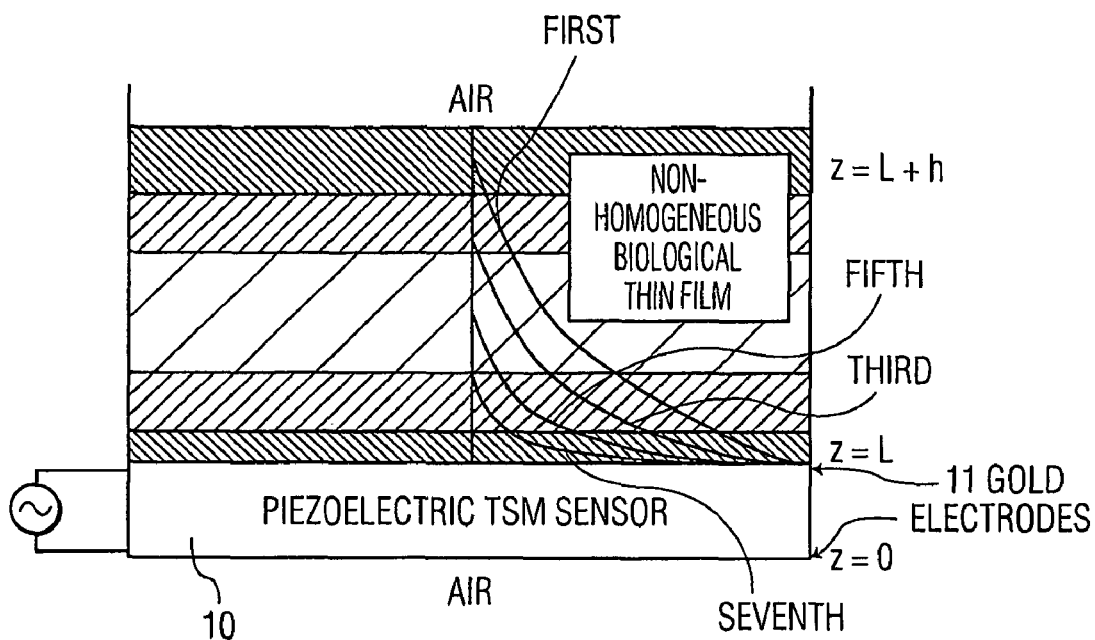
FIG. 6 shows a diagram of a multi-resonant acoustic interfacial analyzer ("MAIA") sensor with a non-homogeneous biological thin film and the different penetration depths achieved using higher harmonics of MAIA.

An important feature of the MAIA is its capability of being excited at high harmonics. As higher harmonics are applied, the information from the responses of the MAIA represents the characteristics of the interfacial area at different distances from the MAIA surface due to the different penetration depths of acoustic waves through the medium. In other words, the medium can be sliced into a multi-layered thin film by applying different harmonic frequencies. FIG. 6 shows the principles of this concept using a piezoelectric MAIA sensor 10 with gold electrodes 11. As shown in FIG. 6 the non-homogeneous biological thin film is split into four layers or regions based upon the first, third, fifth and seventh harmonic of the MAIA.

If, due to the concentration gradient of biological solutes (i.e., collagen monomers or albumin clusters), or aggregation of molecules, the film develops different mechanical properties (i.e., viscosity, density, elastic stiffness) throughout the film thickness during the thin film formation process, it can be analyzed as different responses of the MAIA at different harmonics.

For the example shown, collagens were used. Collagens are a family of highly characteristic fibrous proteins found in all multi-cellular animals. They are secreted by connective tissue cells, as well as by a variety of other cell types. As a major component of skin and bone, they are the most abundant proteins in mammals, making up 25% of the total protein mass in these animals. A typical collagen molecule has a long, stiff, triple-stranded helical structure, in which three collagen polypeptide chains, called a chains, are wound around one another in a ropelike superhelix. So far about 25 distinct collagen a chains have been identified while only 15 types of collagen molecules have been found. Collagen II is the most abundant protein of cartilage and it forms a network of fibrils that are extended by the presence of proteoglycans and thereby provide the resistance of cartilage to pressure.

The example also used albumin. Albumin is the main protein in human blood and the key to the regulation of the osmotic pressure of blood. Chemically, albumins are well known as a class of simple, water-soluble, and heat coagulable proteins. Also they can be found in many animal and plant tissues, especially egg white, blood plasma, serum, muscles, and milk.

During the deposition of a collagen or albumin thin film on the MAIA, there are two major processes involved: evaporation of solution and deposition of proteins on the surface of the MAIA sensor. Initially, the collagen monomers or albumin clusters are homogeneously distributed in the solution, but during evaporation, the concentration of collagen monomers or albumin clusters increases proximate to the surface of the sensor. After reaching a critical concentration, monomers start to aggregate to form large fibrils and clusters also start to form bigger clusters by conglomeration. Then the fibrils and conglomerated clusters sediment on the surface of the MAIA sensor. Finally, when all the solution has evaporated, the collagen fibrils and albumin clusters form a thin rigid film, or a viscoelastic film (VE) on the surface of an MAIA sensor.

Figure 7:
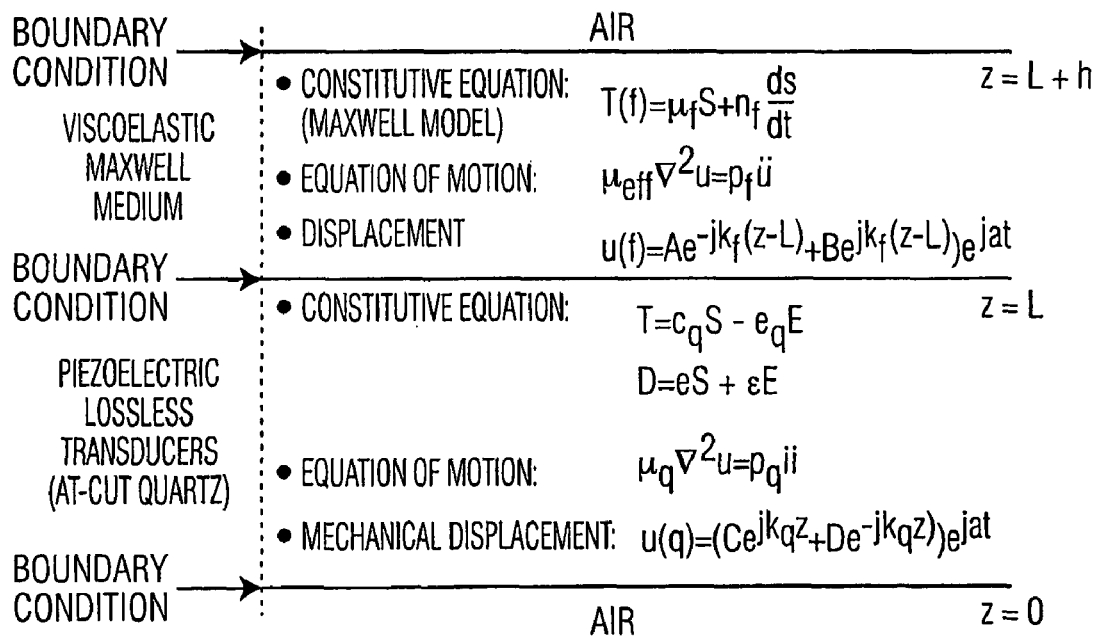
FIG. 7 shows a schematic description of a MAIA sensor that is bio-functionalized, as well as part of the corresponding set of the wave equations and constitutive equations for each layer or region of interrogation for the MAIA sensor.

A simplified model of the system was used to study and analyze the shift in resonant frequency, $\Delta f_r$, as a function of changes in thickness, viscosity and elastic stiffness during the deposition process of the sample. The well-known Maxwell model (two elements of a spring and a dashpot in series) was employed to describe and model the deposition process of the biological sample. New effective complex elastic stiffness, $\mu_{eff}$, which contains an elastic term and a viscosity term, was calculated for the viscoelastic film. FIG. 7 shows the layered structure of an MAIA and viscoelastic sample with boundary conditions at the interface.

First, the constitutive equation of the VE model is, $$T(f) = \mu S + \eta \frac{dS}{dt} = \mu\left(\frac{du}{dz}\right) + \eta \frac{dv}{dz} = (\mu_f + j\omega\eta_f)\frac{du}{dz} \quad \text{(Eq. 1)}$$

If we assume $\mu_{eff} = \mu_f + j\omega\eta_f$, then equation (1) becomes $$T(f) = \mu_{eff} \cdot \frac{du}{dz} \quad \text{(Eq. 2)}$$

where T(f), $\mu$, S, $\eta$, $\mu$, $v$, and $\omega$ stand for stress in film, elastic stiffness, strain, viscosity, displacement, particle velocity, and angular velocity. With the boundary conditions (at z 0, z=L, and z=L+h) at the interfaces between VE film and the MAIA, one can obtain $$\Delta f = \frac{f_{0n}}{n\pi}\tan^{-1}\left(\frac{-k_f(\mu_f + j\omega\eta_f)\tan(k_f h)}{\mu_q k_q}\right) \quad \text{(Eq. 3)}$$

where, $\mu_q$ and $\mu_f$ are stiffness of the MAIA and VE film, and $f_{0n}$, $\Delta f$, h, and $k_q$ are resonant frequency of the MAIA in hertz, the shift in resonant frequency, the thickness of the film, and the wave vector of the MAIA. Wave vector of film, $k_f$, which has real and imaginary parts due to the storage and lossy factor of VE sample, can be rewritten as following, $k_f$=Re$(k_f)$−j(k_f)=k−j$\alpha$: wave vector.

Particle velocity in lossy film can be written as follows:

$$v_f = \left(\frac{\mu_{eff}}{\rho_f}\right)^{1/2} = \left(\frac{\mu_f + j\omega\eta_f}{\rho_f}\right)^{1/2} k_f = \frac{\omega}{v_f} = \omega\left(\frac{\rho_f}{\mu_f + j\omega\eta_f}\right)^{1/2} \quad \text{(Eqs. 4 and 5)}$$

$$k = \text{Re}(k_f) = \omega\left(\frac{\rho_f^2}{\mu_f^2 + (\omega\eta_f)^2}\right)^{1/4}\cos\left(-\frac{1}{2}\tan^{-1}\left(\frac{\omega\eta_f}{\mu_f}\right)\right) \quad \text{(Eq. 6)}$$

$$\alpha = \text{Im}(k_f) = -\omega\left(\frac{\rho_f^2}{\mu_f^2 + (\omega\eta_f)^2}\right)^{1/4}\sin\left(-\frac{1}{2}\tan^{-1}\left(\frac{\omega\eta_f}{\mu_f}\right)\right) \quad \text{(Eq. 7)}$$

It is well known that the quartz crystal is sensitive to changes in interfacial mechanical properties, such as changes in viscosity ($\eta$), density ($\rho$), thickness of the medium (h), elastic stiffness ($\mu$), etc. and the response of MAIA sensor is shown by the changes in resonant frequency ($\Delta f$), attenuation ($\Delta\alpha$), and phase ($\Delta\phi$). Monitoring and studying those responses can measure the mechanical properties of the collagen and albumin thin film. Also, by using the higher harmonic resonant frequencies of the MAIA, the measurand can be monitored within nanometers above the gold surface of the MAIA. In particular, the MAIA can monitor not only viscosity but also elastic stiffness in the medium as a function of time during the deposition process of biological samples.

Figure 8:
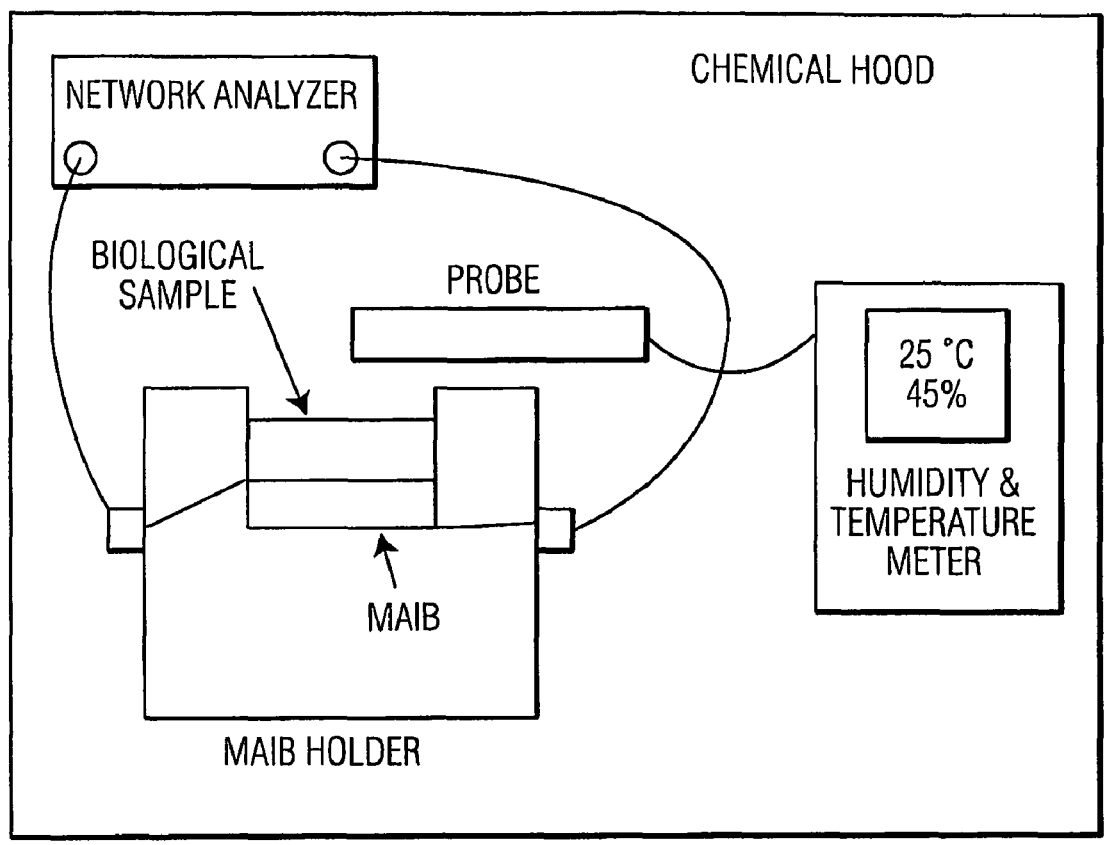
FIG. 8 shows a diagram of an MAIA measurement system with a humidity and temperature meter in a chemical hood.

Generally, the collagen sample is prepared in liquid (water) like phase and finally it ends up with a thin stiff crystallized film and albumin that is also prepared in liquid like phase and ends up with thin viscoelastic (less stiff than collagen and amorphous) film on the gold surface of the MAIA. Therefore, it is important to know the kinetics of deposition process of biological sample as a function of time. The concentration of 50 $\mu$l of 1 mg/ml of acid soluble collagen and albumin samples, and a MAIA with 10 MHz fundamental resonant frequency was used in this example. An MAIA was used to interrogate the VE at $1^{st}$, $3^{rd}$, $5^{th}$, and $7^{th}$ harmonics (approximately 10 MHz, 30 MHz, 50 MHz, and 70 MHz) using a network analyzer and monitored the kinetics and signatures of the deposition process and changes in interfacial mechanical properties of collagen and albumin thin film. As shown in FIG. 8, the network analyzer based computerized measurement system was used. All the measurements were performed in an air flow controlled chemical hood. The temperature was kept at room temperature (approximately 25° C.±3° C.) all the time with humidity approximately 40~50%. A 50 μl of acid soluble collagen or albumin sample was injected on the gold surface of MAIA sensor and the frequency response ($S_{21}$: forward transmission parameters) of the sensor was measured every 30 seconds at each harmonic ($1^{st}$, $3^{rd}$, $5^{th}$, and $7^{th}$) for up to 4 hours.

Figure 9A:
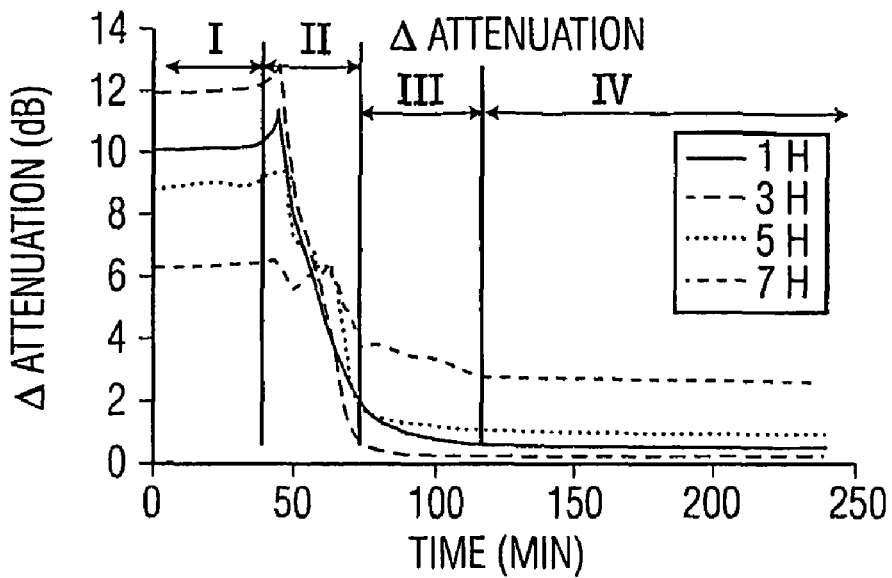
FIGS. 9a-9b show graphs reflecting changes in attenuation of the MAIA sensor interrogating (9a) collagen and (9b) albumin sample as a function of time.
Figure 9B:
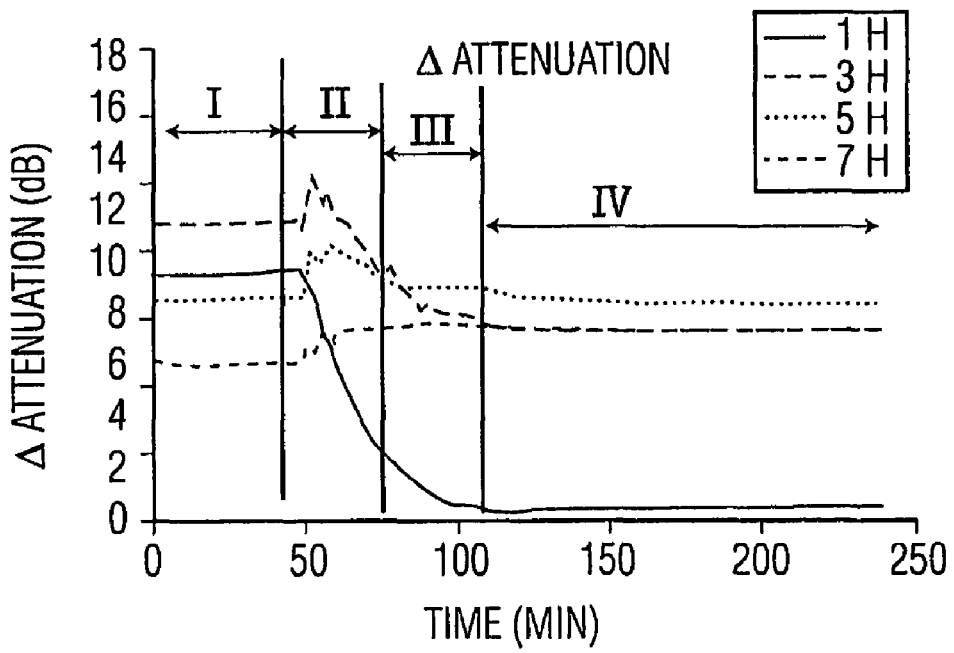

FIGS. 9a and 9b show results of the changes in resonant frequency ($\Delta f_r$) during the deposition of collagen and albumin solution on the gold surface of the MAIA sensor as a function of time at the $1^{st}$, $3^{rd}$, $5^{th}$, and $7^{th}$ harmonics. All graphs show that there are four stages of the MAIA sensor responses during the deposition of collagen and albumin. The first stage (I) is indicated by either a small or by almost no changes in the resonant frequency (0~50 minutes). The injected collagen or albumin samples were in the liquid phase with about 7.5 mm diameter and 1 mm in height from the MAIA sensor surface. During this stage only solvent evaporates and the height of the liquid film decreases because of the evaporation. However, the second stage is rather more complex than the other stages. The first part of the second stage (II-1) is indicated by a sudden increase in the resonant frequency. The sudden increase happens in a very short period of time (less than 5 minutes) in the albumin sample at the $5^{th}$ and $7^{th}$ harmonics. The shape of the sample started to change from liquid to viscoelastic film during this stage. The thickness of the sample decreased to approximately less than 5 μm due to the evaporation of the solvent and left only a gel-type thin film phase on the gold surface of the MAIA sensor, The second part of second stage (II-2) is characterized by a sudden decrease in the resonant frequency. It seems that the entire liquid solution was evaporated at the last moment of this 1'-2 stage and left only a viscoelastic thin film on the MAIA sensor. The third stage (III) is indicated by a small increase in resonant frequency. Finally, the last stage (IV) is shown by a stabilized phase.

It is demonstrated that the MAIA shows the presence of the liquid phase of the film by decreasing the $f_r$ approximately 3 kHz, 7 kHz, 10 kHz, and 15 kHz for each of the harmonics in the first stage for both collagen and albumin. Then, the MAIA shows a period of sudden increase (about 10 and 15 kHz in the $5^{th}$ and $7^{th}$ harmonics of the albumin film) off, in the first part of the second stage (II-1). During this stage (II-1), viscosity and stiffness of the collagen and albumin film change dramatically; there are strong increases in viscosity and stiffness. At the second part of second stage (II-2), $f_r$ decreases by loading the viscoelastic thin film. At the third stage (III) the MAIA shows a small increase in $f_r$ before the final stabilization stage (IV). This is due to the sudden decrease in viscosity with a relatively small increase in the stiffness of the sample. The fourth stage (IV) shows the stabilized condition of the film with relatively small changes in $f_r$.

Figure 10A:
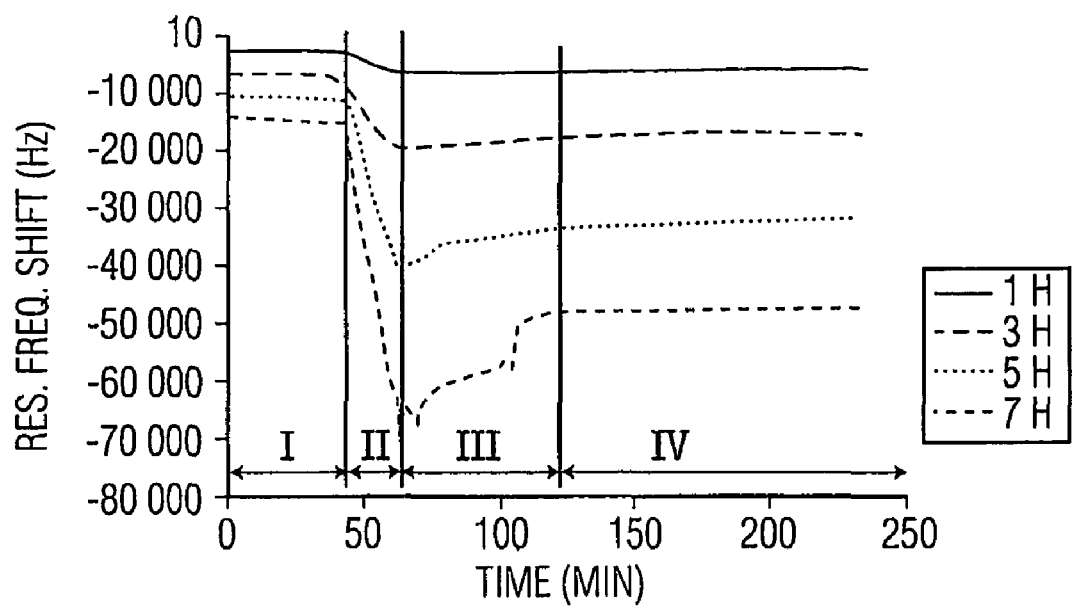
FIGS. 10a-10b show graphs reflecting changes in resonant frequency of an MAIA sensor interrogating (10a) collagen and (10b) albumin film as a function of time.
Figure 10B:
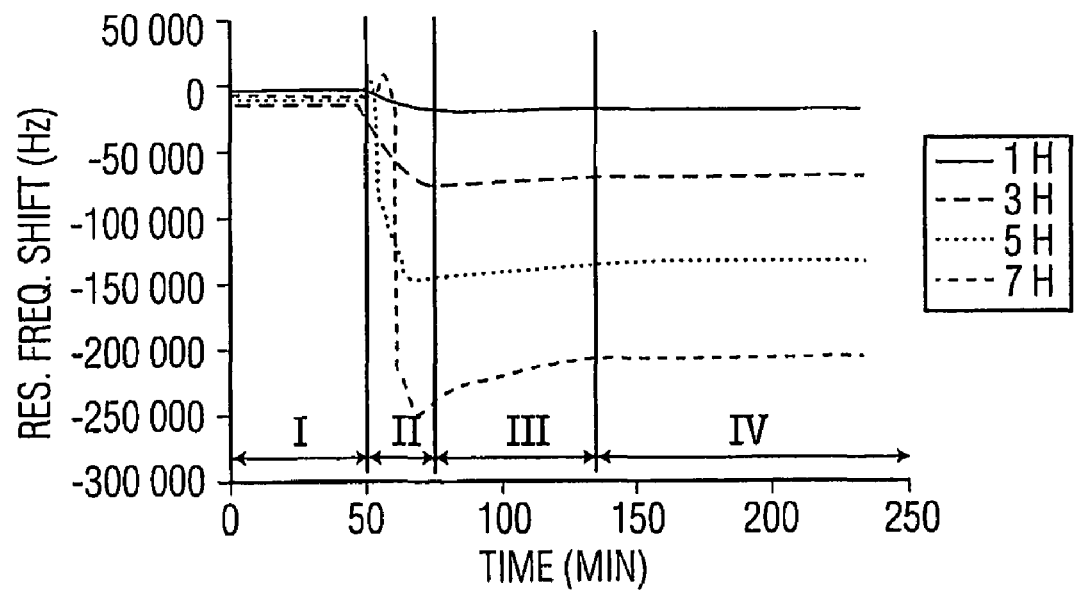

FIGS. 10a and 10b show the preliminary results of the attenuation responses of the MAIA during the deposition of the collagen and albumin thin films. Similar to FIGS. 9a and 9b, both graphs show that there are four stages of the MAIA responses for the deposition process. The first stage (I) is indicated by no change in the attenuation for approximately the first 40 or 50 minutes, and then the first part of second stage (II-1) shows a slight (1~3 dB) increase in attenuation in all the cases. The second part of second stage (II-2) is shown by the sudden decreases in attenuation (steep slope). The third stage (III) is similar to the 1'-2 stage with a decrease in attenuation but differs from the II-2 stage with a rather gentle slope. The last, fourth stage (IV) is indicated by no changes in attenuation or, in other words, stabilized attenuation changes.

Since the different harmonics indicate different depths of penetration of acoustic shear waves into the thin film, differences in the signature of the frequency responses show that the biological thin film has different viscosity and elastic stiffness at different distances from the surface of the MAIA sensor during the deposition process. It is also shown in the example that there are different traces of the viscosity, density, thickness, and elastic stiffness of the sample at different harmonics. Experimental measurements of the viscosity and elastic stiffness of the thin film are difficult during the deposition process, so it can be predicted from the simulation that the viscosity and elastic stiffness of a deposited thin film is higher at the uppermost part and that there are different signatures of changes in viscosity during the phase transition (second stage) at each harmonic.

The example demonstrates an ongoing process that is taking place in collagen and albumin film deposition processes. The model can be improved with support from other measurements of the viscosity, density, elastic stiffness and thickness of the sample film during the deposition process.

Example 2

A Cell-Based MAIA Piezoelectric Sensor

Most biosensors have been based on molecular recognition using antigen/antibody systems, DNA or enzymes. Typically, these types of biosensors are designed for a specific target measurand and provide analytical information, i.e. information on the presence and concentration of a target analyte. In contrast, the use of living cells or tissues offers sensitivity to a broad range of stimuli in the same sensor. These sensors make use of the cells' machinery for signal amplification and provide more global information, which could be related to the way whole organisms like animals or humans may respond to the environment. This last group of sensors, often called functional biosensors, has experienced a rapidly growing interest in recent years, especially in the areas related to environmental testing, drug development, and bioterrorism.

Cell-based functional sensors face unique challenges in their design and development. The cellular component of the sensor is created by introducing into the measurement chamber a suspension of cells. The formation of a mono-layer of cells on the surface is a multi-step process. First, the cells sediment onto the surface of the sensor. Specific bonds are formed between cell surface receptors and extracellular matrix ligands (in this case, serum proteins adsorbed on the sensor surface). The formation of these bonds is resisted by a nonspecific repulsive interaction due to the presence of the cell's glycocalyx. Following the initial adhesive bond formation, the cell will begin to spread. During the spreading process, the cell's shape will change from a sphere with a very small area of contact with the culture surface to a discoid shape with a contact area much larger than the projected area of the original sphere. This shape change is accompanied by a reorganization of the cell's cytoskeleton. Specialized structures called focal adhesions are created. Focal adhesions form anchorage points for bundles of actin filaments and as such are points of mechanical force transmission between the cytoskeleton and the extracellular matrix. The distance separating the cell membrane from the substrate in these regions is 10-15 nm. Elsewhere, the separation distance is in the range of 50-100 nm. The lateral dimensions of the focal adhesions can be up to several microns. The formation and maintenance of focal adhesions is a highly regulated process that is intimately involved with the control of cell growth and differentiation. Although there is continual remodeling of the focal adhesion sites even in an undisturbed cell, their relative area (averaged over a cell) remains nearly constant.

A wide variety of conditions can stimulate the remodeling of the cytoskeleton or an increase or decrease in focal adhesions. Biological agonists can cause either dissolution of the cytoskeleton (usually accompanied by a loss of focal adhesions) or a stiffening and stabilization of the cytoskeleton. Physical stimuli including changes in temperature, pH, or mechanical loading can similarly elicit reorganization of the cytoskeleton or alter the state of adhesion of the cell to its substrate. These structural responses will form the basis for the detection of bioactive agents.

Piezoelectric thickness shear mode MAIA sensors exposed to a liquid produce shear mechanical forces in the form of an acoustic wave. A shear deformation accompanying the wave penetrates into a liquid a short distance from the surface of the sensor. For a typical operating frequency range from 1 MHz to 1 GHz, the penetration depth varies from microns to nanometers. Consequently, the MAIA sensor is very sensitive to interfacial phenomena such as the adsorption of molecules or adhesion of larger particles. It is this feature that is utilized in most piezoelectric chemical and biological sensors. The shear wave penetration depth depends upon the frequency of the wave and on the density and viscoelastic properties of the liquid; thus, the sensor may also be used to monitor these properties of the sample material.

According to an exemplary embodiment of the invention a piezoelectric thickness shear mode sensing technique is used for continuous measurements of interfacial processes involving endothelial cells. Piezoelectric shear-wave sensing technology may offer a unique and potentially a very powerful measurement tool for characterizing a broad range of interfacial processes. Specifically, an interaction of endothelial cells with the gold electrode 11 of an MAIA transducer 10 was examined and the capabilities of MAIA transducers for monitoring vital cell interfacial-processes was evaluated. In addition, due to the fact that biological processes exhibit inherent variability, the MAIA sensors were calibrated with well-characterized physical suspension systems simulating a broad range of interfacial processes. The calibration data allowed for the development of the library of the MAIA signatures corresponding to given interfacial process.

The principles of operating the MAIA will now be discussed. The distribution of shear mechanical displacement generated by a disk-shaped AT-cut quartz shear wave transducer 10a immersed in a Newtonian liquid is given by the classical solution due to Stokes, show graphically in FIG. 11:

$$u = u_0 e^{-\alpha z} \cos(\omega t - \alpha z) \quad \text{(Eq. 8)}$$

The penetration depth, $\delta$, decreases with increasing frequency:

$$\delta = \frac{1}{\alpha} = \sqrt{\frac{2\mu}{\rho\omega}} \quad \text{(Eq. 9)}$$

Figure 11:
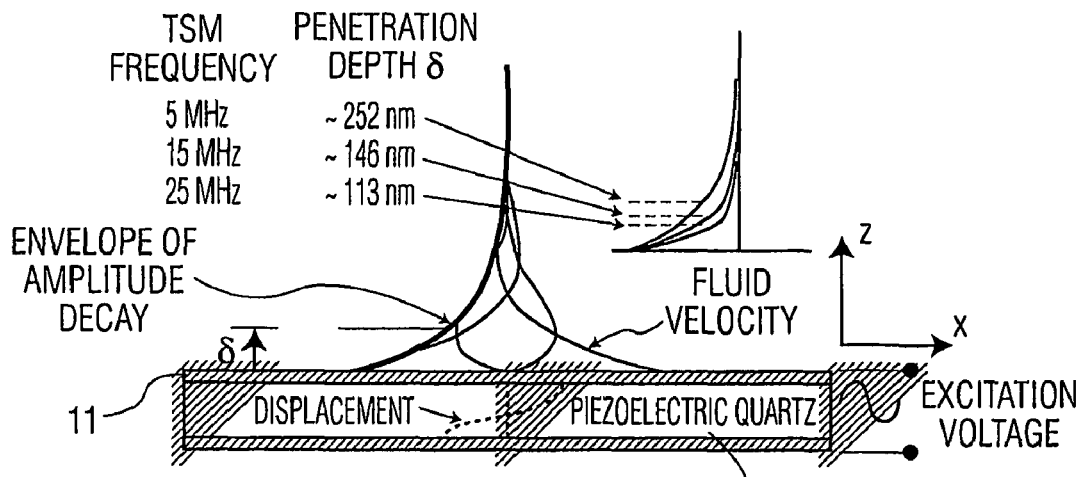
FIG. 11 shows a conceptual model of a piezoelectric MAIA sensing device.

For a 5 MHz crystal operating at its fundamental frequency and higher harmonics, the penetration depth in water varies from tens to hundreds of nanometers. However, an increase of viscosity can significantly extend the depth of penetration to tens of microns. Therefore, if the properties of a liquid medium undergo changes due to chemical or biochemical processes, the depth of penetration may change. In FIG. 11 the velocity profile in the fluid is shown for four quarter-cycle time points within a single cycle of oscillation. The depth of penetration of the oscillating shear wave depends on the viscosity and density of the fluid and the frequency of the sensor oscillation. In the example this phenomena is used to analyze the characteristic length scale of structures at the interface and the dynamically changing mechanical properties of adherent cells.

Figure 12:
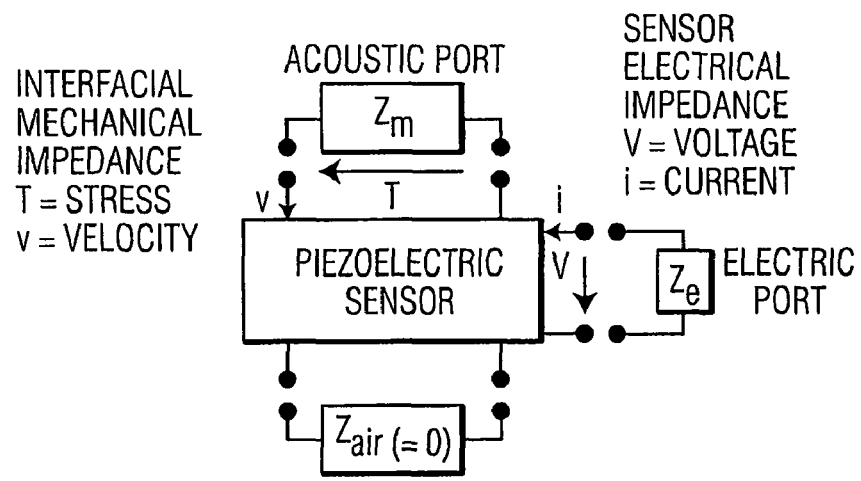
FIG. 12 shows a schematic model of a piezoelectric MAIA sensor with two acoustic ports and one electric port.
Figure 13:
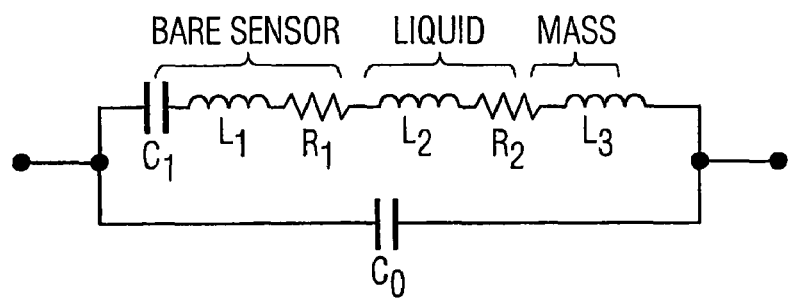
FIG. 13 shows an electric circuit that is the equivalent of the model shown in FIG. 12.

The MAIA piezoelectric sensor can be modeled as a microdevice that transforms mechanical impedance into electrical impedance as schematically shown in FIG. 12. The electromechanical impedance has a resonant character and can be represented in the form of an electric circuit given in FIG. 13. The components of the circuit are related to the properties of the piezoelectric material itself ($C_o$, $L_1$, $C_1$ and $R_1$) and the measured medium ($L_2$ and $R_2$ are related to liquid medium, and $L_3$ describes mass deposition at the surface). For Newtonian liquids, $\omega_s L_2 = R_2 = A \cdot (\rho\eta)^{0.5}$; for viscoelastic media, the expressions are complex. An additional mass (solid phase) accumulation at the interface can be represented as another inductive component $L_3 = B \cdot (\rho_{in})$, where A and B are the sensor constants and $\omega_s$ is the resonant frequency of the sensor.

The sensor response is monitored in terms of the change in magnitude of the resonant peak, which is directly related to the change in motional resistance, $R = (R_1 + R_2)$. Since the motional resistance of the sensor itself does not change, the change in magnitude of the resonant peak can be attributed solely to changes in the motional resistance due to the medium under test ($R_2$).

In the viscoelastic media, the expressions describing the frequency and amplitude changes depend on the type of the medium (Maxwell, Voigt, Burger, etc.). In summary, by monitoring the changes in the resonant frequency and amplitude one can relate them to biophysical processes taking place in cells. For example, if the cells start to proliferate and some structural stiffness builds up in the cell layer, then the viscous losses will be lower, and the frequency will increase and losses will decrease. Therefore, observing the evolution of the sensor characteristics as a function of the time gives insights into the subtle interfacial processes and allows for their biological interpretation.

This process of monitoring sedimentation was demonstrated by suspending carboxylated polystyrene microspheres (1, 10 and 90 µm diameter; Polysciences, Warrington, Pa.) in Dulbecco's Modified Eagles Media (DMEM; Gibco). Suspensions were prepared by diluting the stock solution (2.7% g/ml) 1:5 with tissue culture medium DMEM. Final concentrations of spheres were $9.8 \times 10^9$, $9.8 \times 10^6$, and $13.5 \times 10^3$ spheres/ml, respectively. Suspension samples were agitated just prior to their placement in the chamber to ensure a uniform dispersion of particles.

In the example, the measurements were performed using the MAIA sensors operating at the fundamental resonant frequency of 5 MHz and the odd harmonics of 15 and 25 MHz. The MAIA frequency responses ($S_{21}$ scattering parameter) were measured using a HP 8595 Network Analyzer based measurement system, which provided the resonant frequency and amplitude of the sensor as a function of time. Typically the measurements were performed over a 1-hour period, with data recorded every minute. Measurements were repeated at least 3 times to determine the accuracy and repeatability of the results. A measurement cell was specially designed for studying suspension samples. The cell measurement compartment was a cylindrically shaped with the diameter of 6 mm and the height of 8 mm. The height of the suspension medium during the experiment was 5 mm.

Bovine Aortic Endothelial Cells (BAECs) are isolated from calf ascending aorta. The cells are subcultured in DMEM and supplemented with 10% heat-inactivated calf serum (Gibco), 2 mmol/L L-glutamine (Gibco), 100µ/ml penicillin and 100 g/ml streptomycin (Gibco), and 10 mM N-2-hydroxyethylpiperazine-N'-2-ethanesulfonic acid (HEPES; Sigma), maintained at 37° C. in 5% $CO_2$ in air and fed every 2-3 days until confluent. The MAIA measurement chamber was sterilized by thoroughly rinsing the culture surface and chamber with ethyl alcohol followed by drying and exposure to UV light. The size of the culture chamber was designed to accommodate the lids of standard tissue culture Petri dishes. Cells were plated onto the surface using standard techniques performed sterilely in a laminar flow hood. For long-term experiments, the MAIA chamber was kept in a humidified, 37° C. incubator with 5% $CO_2$ in air. Leads for the electronics were threaded through ports on the incubator. For short-term sedimentation, adhesion and spreading experiments, the cell suspensions were added to the chamber that is already connected to the analyzer and recording continuously. The volume of the suspension added was kept constant for all experiments so as not to influence the sedimentation time. All these liquid sample preparation steps were monitored by the MAIA in order to evaluate their influence on the sensor response.

To relate MAIA measurements of cellular responses to changes in the environment, it is necessary to understand the microstructural correlates of the MAIA signals. Since the behavior of cells at interfaces is complex, a physical model system was used to characterize the sedimentation process and to evaluate the ability of the sensor to detect structural features of different characteristic length scales.

The sedimentation of polystyrene microspheres was monitored as a function of time using three different operating frequencies of the MAIA sensor. During sedimentation, the layer adjacent to the sensor surface gradually becomes filled with spheres. In addition, the concentration of spheres increases such that the effective viscosity of the suspension may be altered. The changing number of spheres touching the surface of the sensor and the increasingly strong interaction between spheres in the suspension can be expected to influence sensor readings.

The size of the spheres influences both the sedimentation rate and their spatial arrangement at equilibrium. In dilute suspensions the sedimentation velocity depends on the diameter of the spheres, the difference in density between the suspending fluid and the spheres, and the viscosity of the suspending fluid. For a given fixed volume fraction of the solid particle phase, the number of spheres and the thickness of the final sediment layer varies with the sphere diameter. It is possible to estimate the time required to fill a single layer of spheres on the sensor surface based on sedimentation rate and concentration (Table 1). Accumulation of polystyrene spheres at the MAIA surface causes quite strong and distinct changes in the resonant amplitude with a characteristic time constant that corresponds to the predicted time to fill a single layer of spheres on the surface (shown in FIGS. 14a-14c).

Figure 14A:
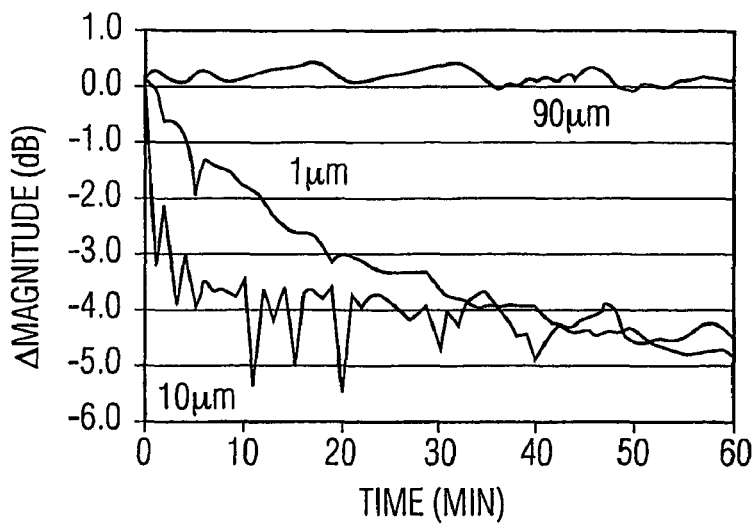
FIGS. 14a-14c show graphs of the sedimentation of polystyrene beads monitored at three different frequencies, (14a) 5 MHz, (14b) 15 MHz, and 14(c) 25 MHz.
Figure 14B:
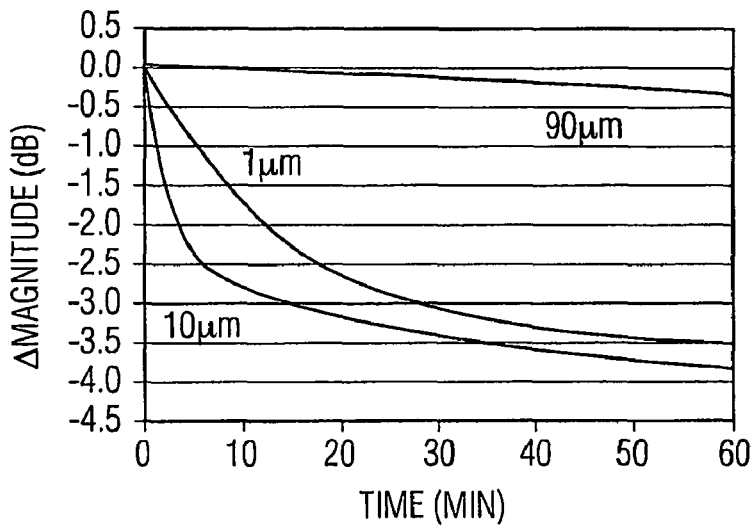
Figure 14C:
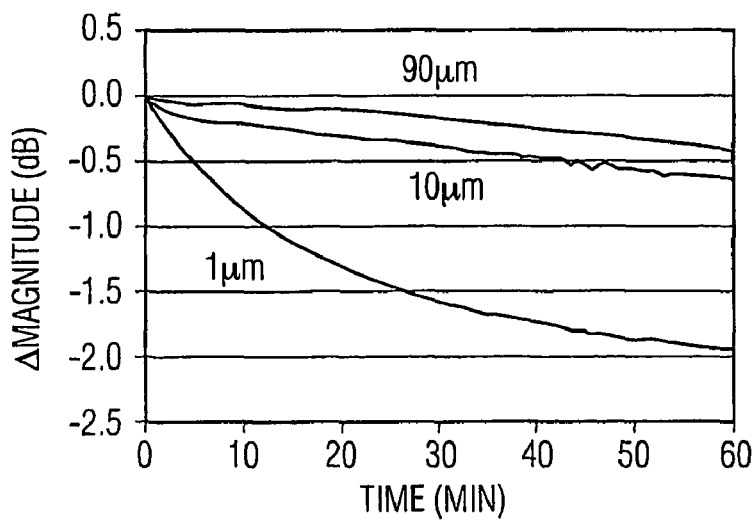

The relationship between the penetration depth and the characteristic length scale of the structure at the interface is demonstrated by monitoring the sedimentation process using three particle sizes with three frequencies and, therefore, three penetration depths as shown in FIGS. 14a-14c. The sedimentation kinetics of the 1.0 µm particles is accurately detected at all three operating frequencies. In contrast, the 10 µm particles are only detected at the lower two frequencies corresponding to greater penetration depths. The largest particles (90 µm) were not detected at any of the frequencies. This can be explained by the fact that the solid volume fraction within the layer defined by the penetration depth of the shear wave varies inversely with sphere diameter and is less than 1% for the 90 µm particles even for the lowest frequency tested.

TABLE 1

| Diameter (µm) | Vs (cm/s) | h* (cm) | t* (min) |
|---|---|---|---|
| 1 | $3.1 \times 10^{-6}$ | 0.01 | 128 |
| 10 | $3.1 \times 10^{-4}$ | 0.1 | 12.8 |
| 90 | $2.5 \times 10^{-2}$ | 1 | 0.14 |

It should be noted that the effective viscosity of the suspension depends strongly on the volume fraction of the solid particles as the particles accumulate on the surface. Thus, the penetration depth of the acoustic wave may become much larger than the values given for pure water. This phenomenon will also contribute to the kinetics of the sensor response and may explain the biphasic response of the 10 µm spheres, i.e., the initial rapid change may be due to the filling of the first layer of spheres, whereas the secondary slower change may represent increase in viscosity due to the consolidation of additional layers of spheres. For the 1.0 µm spheres, Brownian motion of the particles can be expected to play a role in the kinetics of sedimentation and the final concentration distribution. Rather than forming multiple layer of uniform concentration, the spheres would reach a continuous distribution of concentration decaying roughly exponentially away from the surface.

Figure 15A:
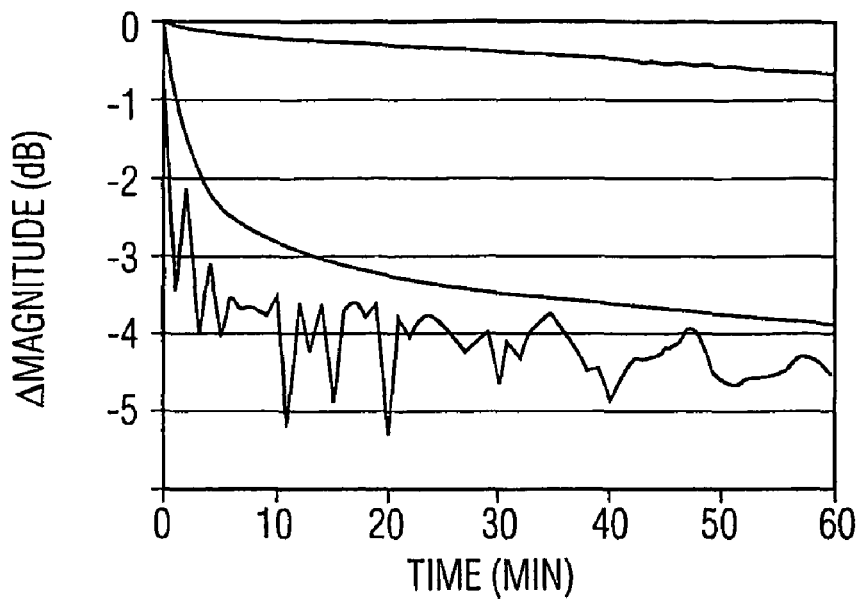
FIGS. 15a-15b show graphs of changes in the MAIA sensor response accompanying sedimentation and initial attachment of endothelial cells on a gold surface at 5, 15, and 25 MHz.
Figure 15B:
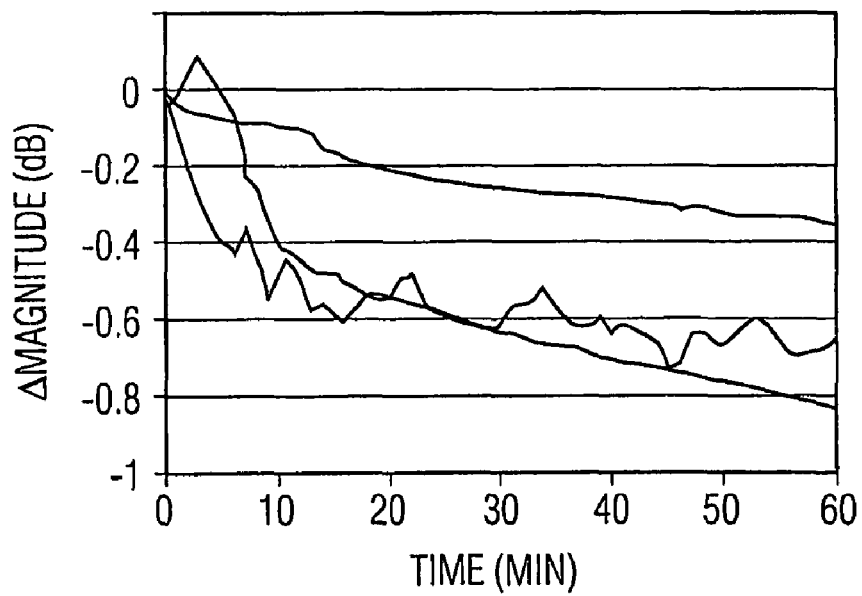

These experiments demonstrate that by probing the medium at different depths, events can sensitively be monitored or structural changes at the interface can be used to distinguish between signals due to structures located at different distances from the sensor surface. The same approach was used to characterize the interaction of living endothelial cells with the sensor surface. The sedimentation of bovine aortic endothelial cells (BAECs) was measured by placing a suspension of cells on the sensor and monitoring the signal at 5, 15 and 25 MHz for 1 hour, as shown in FIG. 15a. The kinetics of sedimentation were similar to the 10 µm polystyrene spheres, which are of a size and density (1.05 g/ml) similar to the endothelial cells. The 5 MHz experiment with cells shows only the sedimentation phase of the response (t<10 minutes). However, the shorter penetration depths of the 15 and 25 MHz excitations revealed evidence of an active biological process evolving over time and not present in the polystyrene sphere experiments. The decrease in the magnitude of the 15 MHz resonance feature peak resembled that for the microspheres, but with a delay of 5 minutes. Similarly, the MHz signal dropped significantly at 15 minutes (as shown in FIG. 15b). A decrease in magnitude indicates an increase in the viscous loss. The timing of the decrease in magnitude at successively shorter penetration depths may indicate sequential steps in the cell adhesion process including the establishment of adhesive bonding between the cells and the substratum (overcoming nonspecific repulsion) and, perhaps, the initial spreading of the cells. The magnitude of the 15 MHz resonance feature peak dropped significantly at approximately 20 minutes (FIG. 15b). A decrease in magnitude indicates an increase in the viscous loss. Since the penetration depth is only 100 nm, it is hypothesized that the large drop in magnitude at 20 minutes represents the establishment of adhesive bonding between the cells and the substratum and, perhaps, the initial spreading of the cells.

Sedimentation of cells and spheres onto MAIA sensor surfaces has been studied typically by monitoring changes in the resonant frequency indicating mass loading of the sensor. When the kinetics of the response are shown in detail, there appears to be a delay in the response following the initial inoculation of the chamber similar to the delayed response observed in the 15 and 25 MHz signals.

Figure 16:
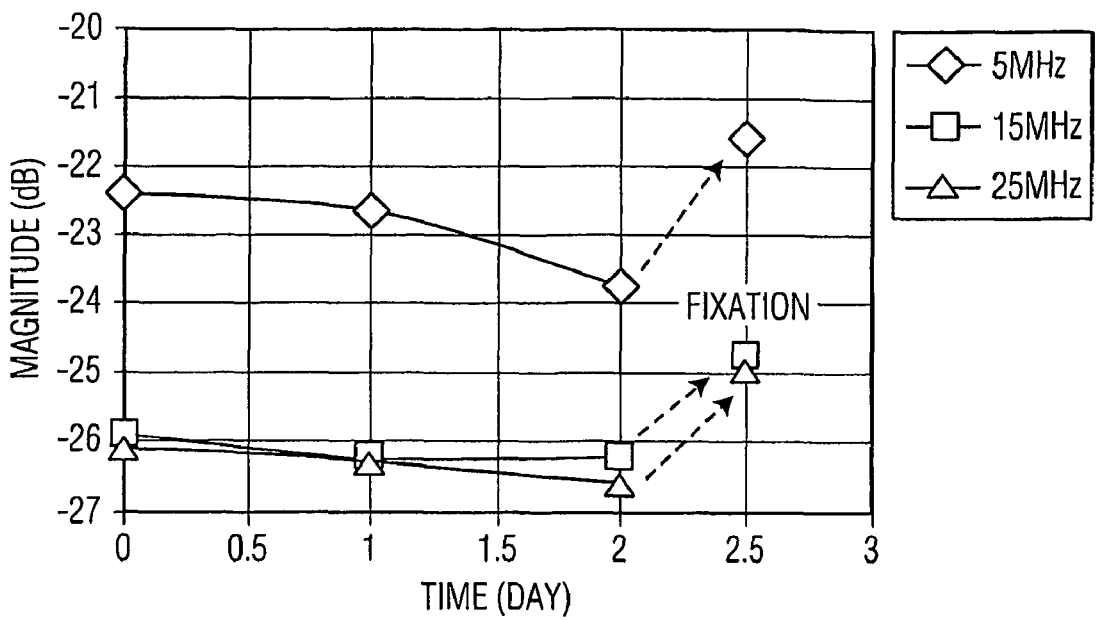
FIG. 16 shows a graph depicting a simulation of cell death by fixing cells with formaldehyde.

To test the sensitivity of the sensor to the subtle changes in morphology with time in culture, BAECs were plated on the sensor at a slightly subconfluent density and monitored for two days. After reaching confluence, BAECs tend to lose their actin stress fibers in favor of a cortical arrangement that appears as a peripheral band along the cell junctions. The decrease in the 5 MHz resonance feature peak magnitude may represent this loss of structure in the region of the cell adjacent to the substrate, as shown in FIG. 16. To verify that this technique indeed reports mechanical properties, the cells were fixed with formaldehyde. The crosslinking of cellular proteins causes the cell to stiffen and to behave more elastically with less viscous loss. The increase in magnitude of the resonance feature peak is consistent with this interpretation.

This example shows the use of MAIA sensors for the development of cell-based biosensors. The example has demonstrated the ability of the sensor to detect and distinguish interfacial structures of different characteristic length scales and material properties. In particular, such interfacial processes as sedimentation, attachment and proliferation can be measured in real time with high time resolution on the order of seconds. MAIA cell-based sensors can be used for monitoring a variety of interfacial phenomena in non-uniform biological media in real-time. The sensors can be used for broad applications in the medical, pharmaceutical and chemical industries. MAIA sensors can also provide a viable technique for laboratory-based measurement instrumentation useful for the characterization of cell interfacial processes.

Example 3

Suspensions with MAIA Piezoelectric Sensors

Suspensions play an important role in numerous chemical, biochemical and biological processes. Industrial liquid media such as paints and clays, or biological fluids such as blood, proteins and nucleic acids in solutions, etc. exhibit suspension-unique features, which allow them to perform complex functions and operations. In the biological world these specific features of suspensions support many life-important processes. For example, monitoring an interaction of blood (which is a suspension of red cells in a water-based protein rich fluid) with blood vessels provides valuable information relating to the transport of oxygen, nutrients and waste in animals.

The properties of suspensions are strongly influenced by interfacial processes caused by a high surface to volume ratio of a suspended phase. Generally, one can distinguish two kinds of the interfaces of interest. The first type of interface is created by a suspended phase (usually in a form of solid-like particles) and a suspending phase (usually a liquid). The second type of the interface is formed by a suspension and a surface of solid materials. The last case, which is the focus of this example, involves interfacial processes in surgical implants, biosensors, and biochips, etc.

The MAIA-based measurement technique is very simple, inexpensive, sensitive and accurate and allows quantitative continuous measurements of interfacial processes involving suspensions in real time. Piezoelectric shear-wave sensing technology offers a unique and very powerful measurement tool for characterizing interfacial processes.

Piezoelectric MAIA sensors exposed to a liquid produce forces that propagate through the liquid in the form of acoustic waves. A shear deformation accompanying the wave penetrates into a liquid at a short distance from the surface of a sensor. This last feature is very favorable because it makes a MAIA sensor sensitive to interfacial phenomena, and this feature is utilized in most piezoelectric chemical and biological sensors. The shear wave penetration depth depends on the frequency of the wave, and the density and viscoelastic properties of the liquid.

Figure 17:
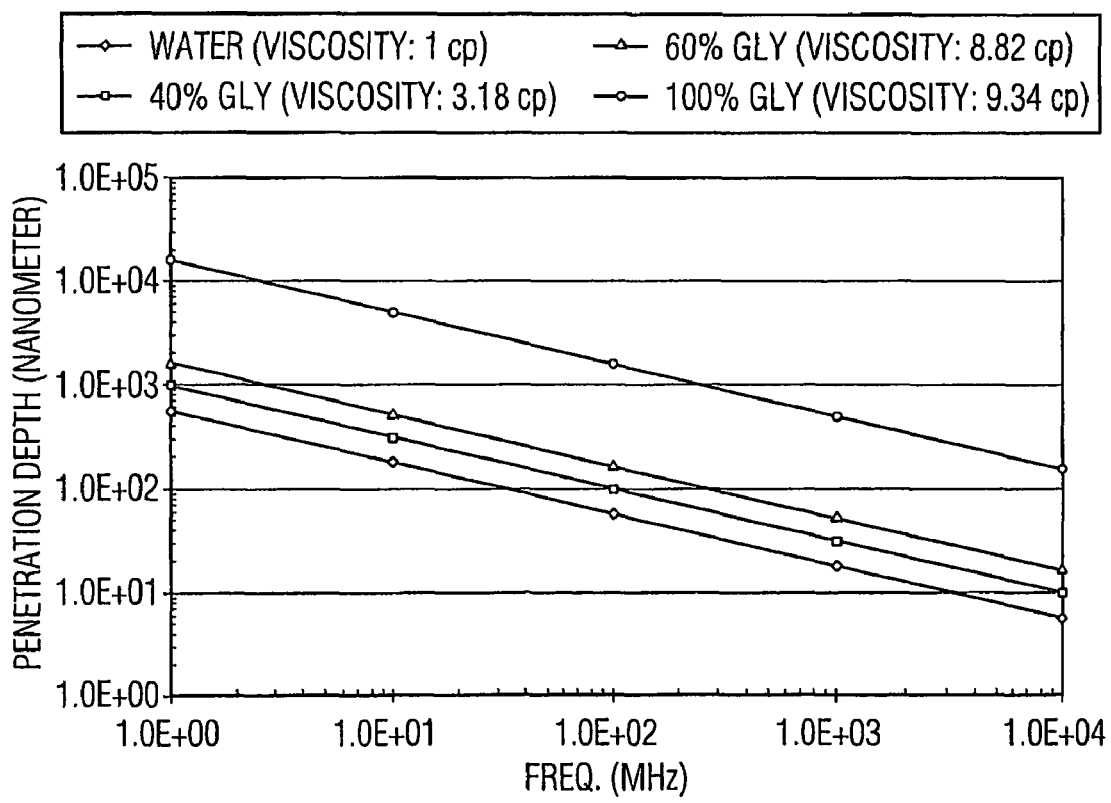
FIG. 17 shows a graph of the penetration depth of a shear acoustic wave as a function of frequency for several water-glycerol solutions of different viscosities.

In FIG. 17 the penetration depth as a function of frequency for water and water-glycerol solutions is depicted for the frequency ranging from 1 MHz to 1 GHz. Water is probed over a relatively short distances extending from tens to hundreds of nanometers. However, an increase of viscosity can significantly extend the depth of penetration to tens of microns. Therefore, if the properties of a liquid medium undergo changes due to chemical or biochemical processes, the depth of penetration may change. As a result the wave probing depth will dynamically change on probing either a thicker or thinner layer of an adjacent medium. This fact is important in analyzing the interaction of suspensions with MAIA surfaces because in many cases interfacial processes involving suspensions are strongly time dependent. As a result, the properties of a layer adjacent to the MAIA surface may change significantly as well as the spatial distribution of suspended and/or adhered solid phases. Because the depth of penetration depends on the frequency of a sensor, choosing a right operating frequency is important when analyzing suspensions.

In the case of uniform media, the choice of the magnitude of the operating frequency usually is considered from the point of view of measurement accuracy and sensitivity. In suspensions, which are nonuniform media, especially at the interfaces, a primary factor determining the operating frequency should include the fact that at different frequencies different features of a suspension may be monitored. This feature can be advantageously applied for the study of a broad range of important suspension interfacial phenomena.

Figure 18A:
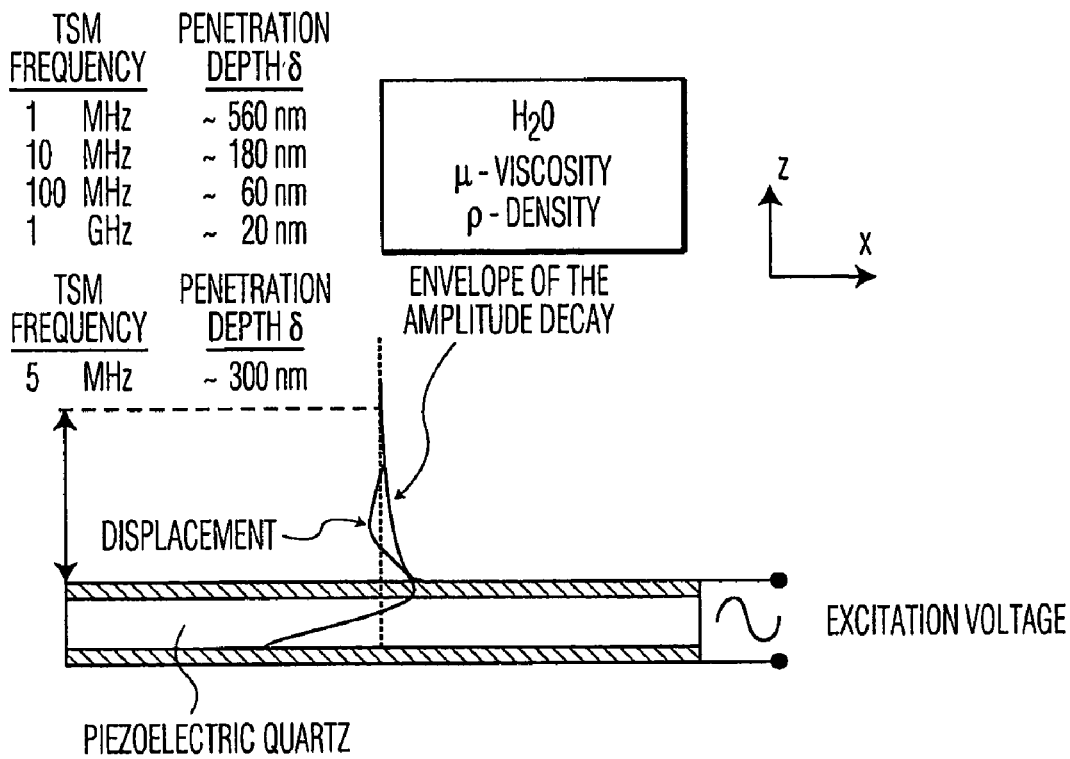
FIG. 18a shows a sensor operating at the fundamental frequency.
Figure 18B:
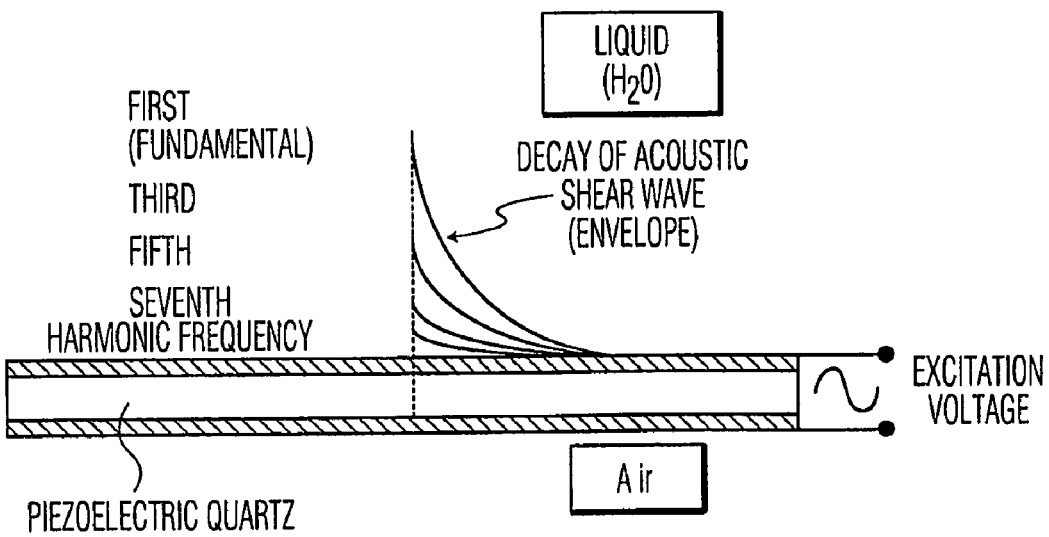
FIG. 18b shows a sensor operating at the fundamental frequency and at higher harmonics.

An advantageous material for fabrication of MAIA sensors is quartz. Quartz is chemically inert, has superior mechanical properties and is temperature compensated. AT-quartz cut orientation is useful for the fabrication of MAIA-based resonator sensors. In FIGS. 18a and 18b, a schematic presentation of a distribution of shear mechanical displacement generated by a disk-shaped AT-cut transducer immersed into a Newtonian liquid, such as water, is given when the transducer operates at the fundamental (a) and harmonic frequencies (b). One can consider a piezoelectric sensor operating sequentially at its harmonic frequencies as a "slicing probe" monitoring an interface at different depths, shown in FIG. 18b, hence providing important spatial information about a suspension and ongoing physico-bio-interfacial chemical processes. In the analyzed suspensions these frequency-dependent features are clearly present. In an exemplary embodiment, a MAIA sensor operating at its fundamental frequency $f_r=5$ MHz and its harmonics $f_{r2}=15$ MHz and $f_{r3}=25$ MHz was employed.

Figure 19A:
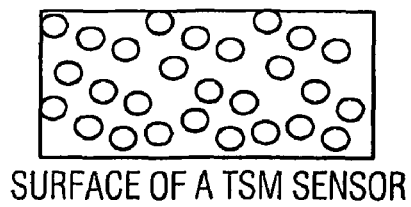
FIG. 19 shows the spatial distribution of polystyrene spheres in a sedimentation and packing experiment, (a) in the initial, uniform state, (b) in an intermediate distribution, and (c) in a final distribution.
Figure 19B:
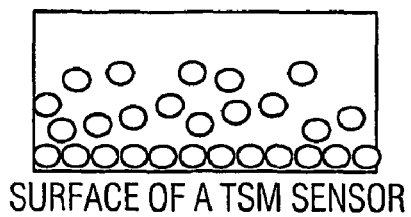
Figure 19C:
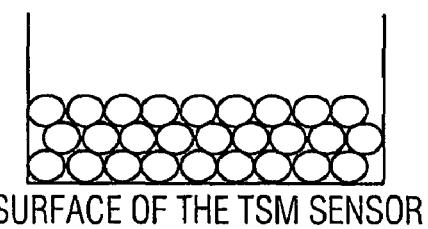
Figure 19C:

The studied suspensions consisted of polystyrene spheres of the size 1, 10 and 90 microns, respectively, suspended buffered saline solution (DMEM). The DMEM is routinely used for cell culture and cell suspensions. The concentration of the suspension defined as a volume sphere solution of a given diameter over the total volume of the suspension was 2.7% solid. The performed experiments involved monitoring the sedimentation process as a function of time measured at different operating frequencies of a MAIA sensor. During the sedimentation process a distribution of sphere arrangements underwent changes. In FIGS. 19a-19c, a sketch of the polystyrene suspension taken at three different times representing a possible distribution of the spheres is depicted. FIG. 19a pictures an initial state when the suspension is uniform. Next, FIG. 19b represents an intermediate situation, and FIG. 19c the final state. These pictures show that the density and viscoelastic properties of the suspension significantly change with time. Also, the mechanism of an interaction between suspended particles and the surface of a MAIA sensor varies as well. In particular, the medium with separate non-interacting spheres approaches a highly concentrated suspension with a strong interaction between spheres.

Figure 20A:
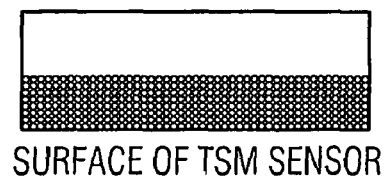
FIG. 20 shows the final spatial distribution of spheres in a measurement cell as shown in FIG. 19, part (c) for three different sized spheres, (a) 1 micron spheres, (b) 10 micron spheres, and (c) 90 micron spheres.
Figure 20B:
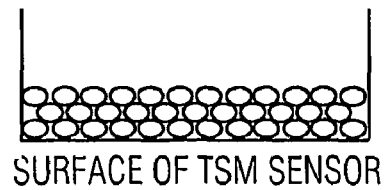
Figure 20C:
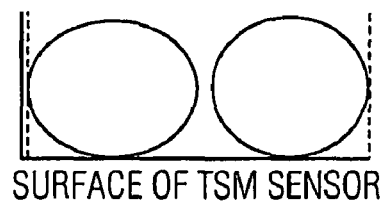

The size of the spheres also influences their spatial arrangement. For a given fixed concentration of a solid particle phase, the number of spheres strongly varies with the sphere diameter. As a result, the thickness of the final sediment layer is sphere diameter dependent. In FIGS. 20a-20c, sketches of the final sphere distribution for 1, 10 and 90 micron diameter spheres are given. These distributions are drawn for a fragment of the actual geometry and dimensions of the MAIA sensor and measurement cell. FIG. 20a shows that there is approximately 10 layers of the 1 micron spheres evenly distributed along the surface of the MAIA sensor. FIG. 20b shows 3 layers of 10 micron spheres. FIG. 20c shows one incomplete layer of 90 micron spheres.

The measurements were performed using the MAIA sensors operating at the fundamental resonant frequency of 5 MHz and the odd harmonics of 15 and 25 MHz. The MAIA frequency responses ($S_{21}$ scattering parameter) were measured using a HP 8595 Network Analyzer based measurement system, which provided the resonant frequency and amplitude of the sensor as a function of time. Typically, the measurements were performed over a 1-hour period, with data recorded every minute. Suspension samples were handled very carefully and the measurements were repeated at least 3 times to determine the accuracy and repeatability of the results. A measurement cell was specially designed for studying suspension samples. The cell measurement compartment was cylindrically shaped with the diameter of 6 mm and the height of 8 mm. The height of the suspension medium during the experiment was 5 mm. The measured suspension parameters included the sedimentation rate, and the changes of the suspension properties as a function of time, concentration and the penetration depth of the probing acoustic wave.

(i) 1 Micron Polystyrene Sphere Suspension

Figure 21A:
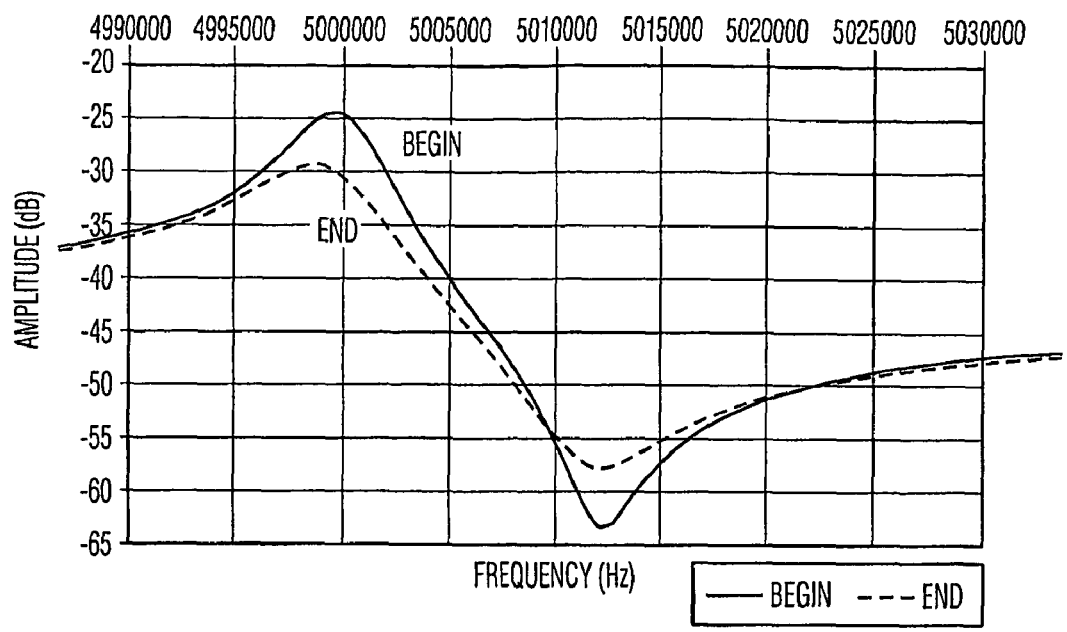
FIGS. 21a-21c show graphs of the MAIA frequency response ($S_{21}$) at the beginning (top curve) and the end of the sedimentation and packing experiment for 1 micron spheres (after 60 minutes—bottom curve) as a function of frequency taken at (21a) 5 MHz, (21b) 15 MHz and (21c) 25 MHz.
Figure 21B:
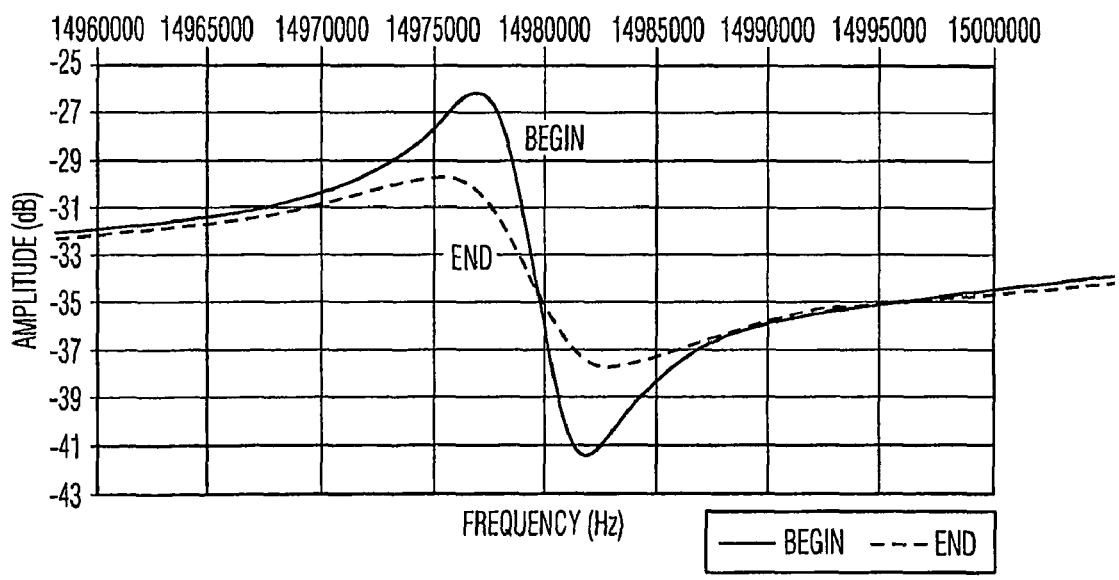
Figure 21C:
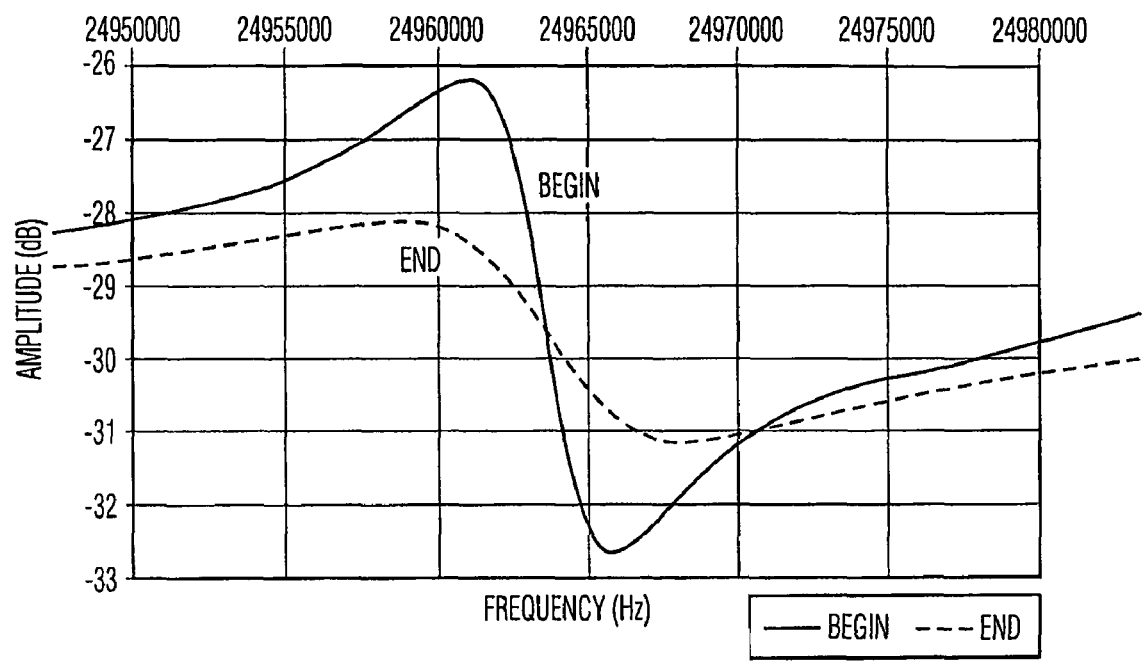

Several experiments were conducted at 5, 15 and 25 MHz each for an hour. FIGS. 21a-21c show the changes in sensor frequency and amplitude response time at the beginning and at the end of each experiment when an initially uniform suspension becomes more and more concentrated at the interface and the particles begin to arrange themselves into a given interfacial sphere structure.

FIGS. 21a-21c show the effects that the 1 μm polystyrene spheres' sedimentation and packing have on the 5, 15 and 25 MHz MAIA response. This type of the response was expected in this case. It is clear from the simple analysis of the sedimentation process (see FIGS. 19 and 20) that the suspension interfacial density and viscosity should increase with time, and as result a decrease in the resonant frequency and the increased attenuation should be observed.

(ii) 10 μM Polystyrene Sphere Suspension

Figure 22A:
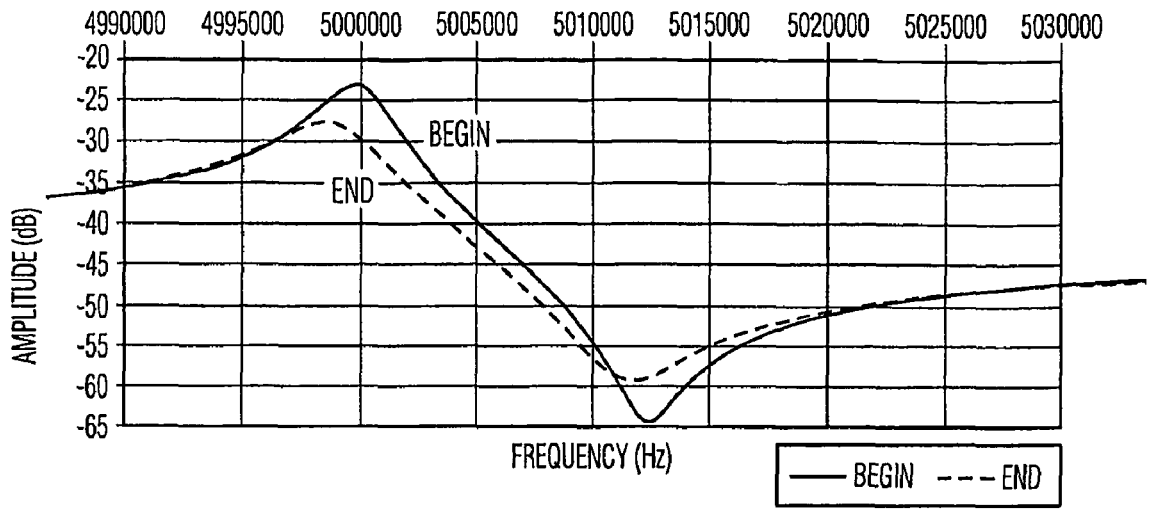
FIGS. 22a-22c show graphs of the MAIA frequency response ($S_{21}$) at the beginning (top curve) and the end of the sedimentation and packing experiment for 10 micron spheres (after 60 minutes—bottom curve) as a function of frequency taken at (22a) 5 MHz, (22b) 15 MHz and (22c) 25 MHz.
Figure 22B:
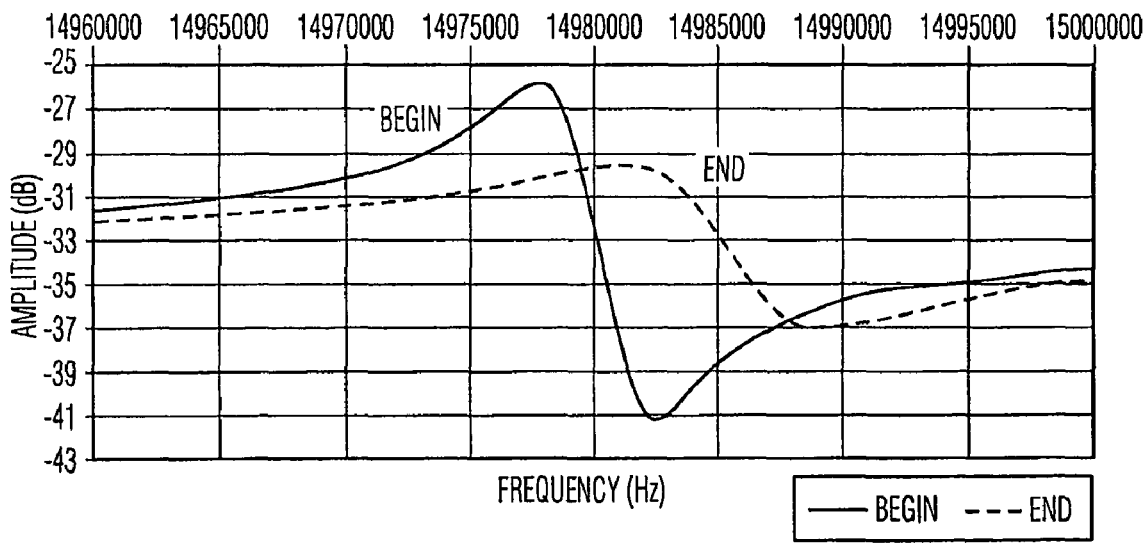
Figure 22C:
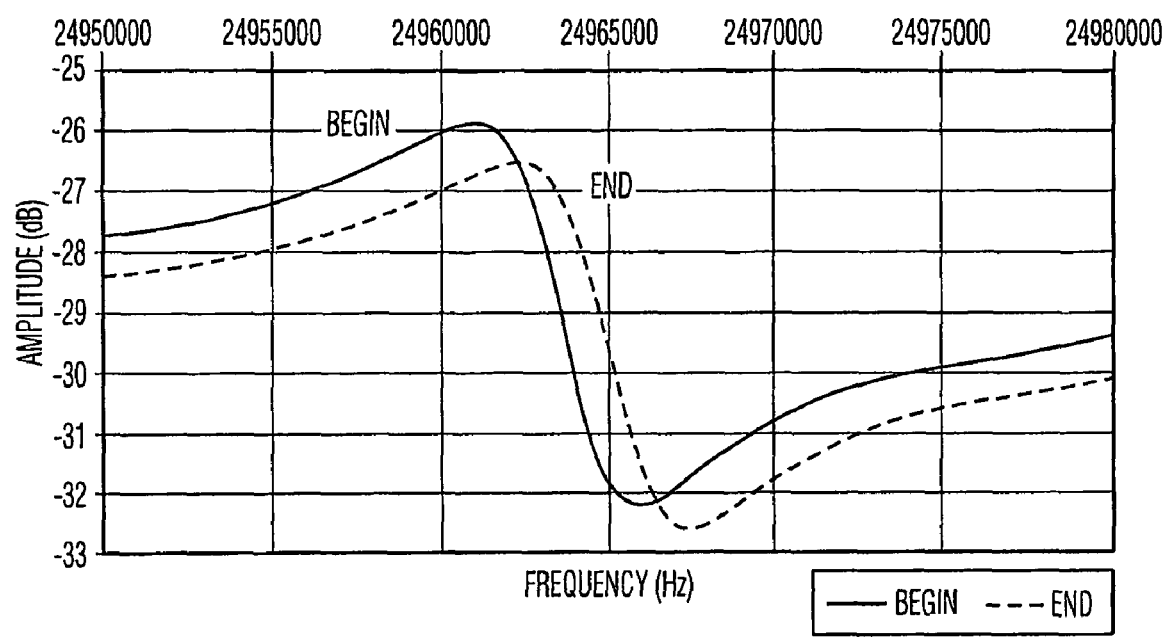

Similar experiments to the 1 μm spheres were conducted using the 10 μm polystyrene spheres. FIGS. 22a-22c show the changes in resonant frequency and amplitude in time. In this case, in comparison to 1 micron spheres, a similar dependence was obtained at 5 MHz, but very different behavior in the sensor response was observed at 15 MHz and 25 MHz. At 5 MHz (FIG. 22a) the sensor response is typical for a viscous/viscoelastic medium. However, at 15 MHz (FIG. 22b) and 25 MHz (FIG. 22c) the end-experiment curves were (after 60 minutes) shifted to the right with respect to the beginning-experiment curves. This shift can be explained by a resonant type of interaction between the suspended spheres and the MAIA sensor.

The increase in resonant frequency is observed also when a MAIA sensor is loaded with thin film having thickness is close to the half-acoustic wavelength. One may then claim that the particles at the interface form the acoustically distinguished layer, which the presence provides a resonant interaction mechanism. In the analyzed case there is likely a mix of both these conditions, but with a dominant factor of the resonant particle-surface interaction. A simple calculation of the bonding energy between the 10 micron suspended polystyrene particles and the MAIA gold sensor surface provide value k=29 [dyne/cm]. It is interesting to mark that the strength of the resonant interaction is weaker at 25 MHz then at 15 MHz. (Notice the same frequency scale for the three graphs in FIGS. 22a-c, and the same amplitude scale for 15 and 25 MHz.). Also, one can observe a substantial dumping of the sensor signal. The dumping is the strongest at 15 MHz at which the measured frequency shift was the largest one. It suggests that some frequency dependent dissipative mechanisms involving the transmission and/or absorption of acoustic energy are present at the interface.

(iii) 90 μM Polystyrene Sphere Suspension

Figure 23A:
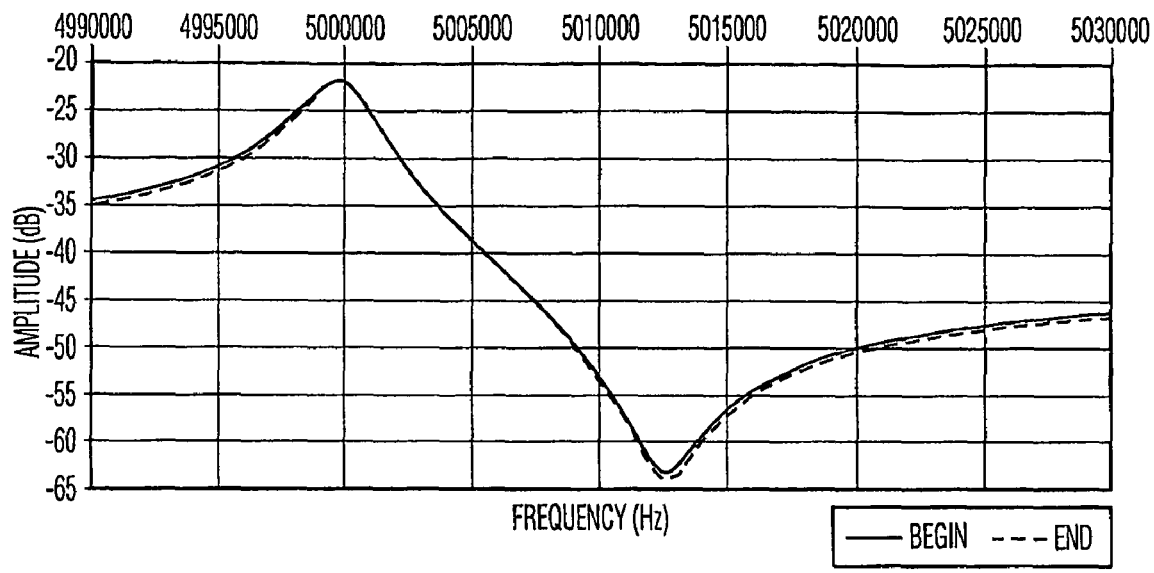
FIGS. 23a-23c show graphs of the MAIA frequency response ($S_{21}$) at the beginning (top curve) and the end of the sedimentation and packing experiment for 90 micron spheres (after 60 minutes—bottom curve) as a function of frequency taken at (23a) 5 MHz, (23b) 15 MHz and (23c) 25 MHz.
Figure 23B:
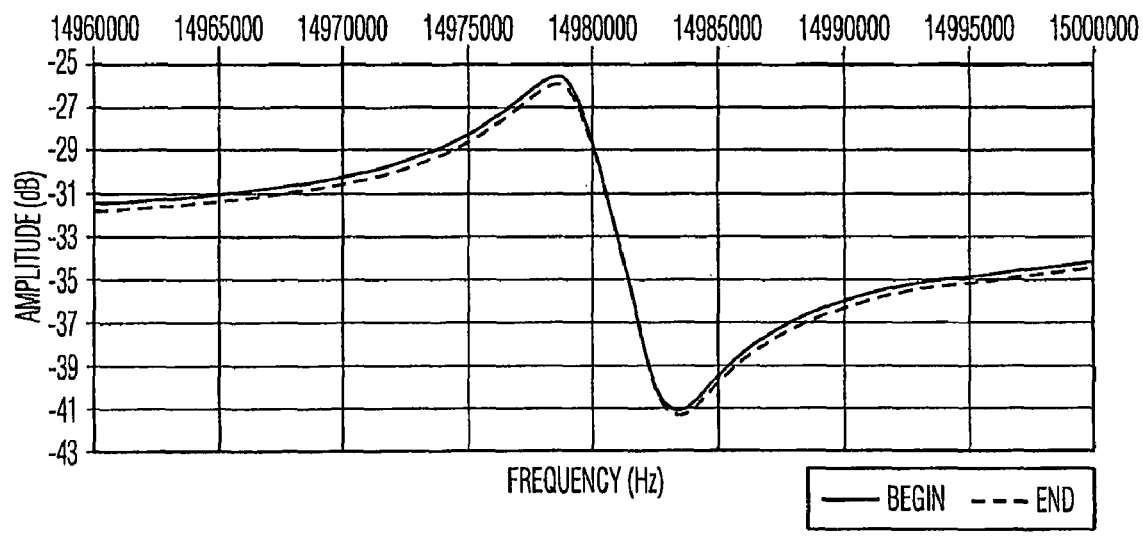
Figure 23C:
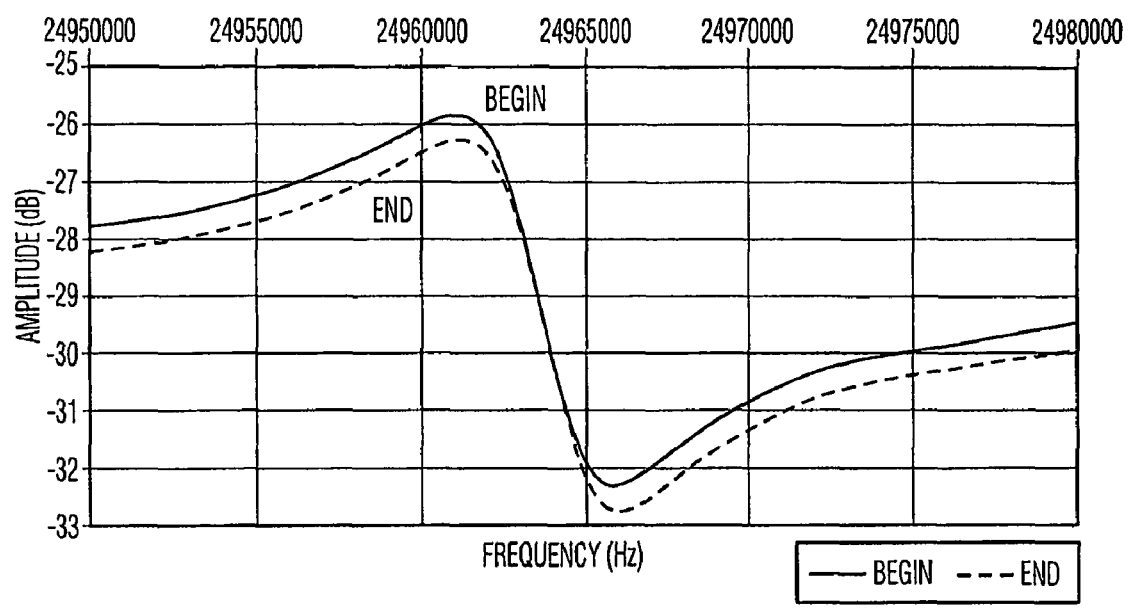
Figure 24A:
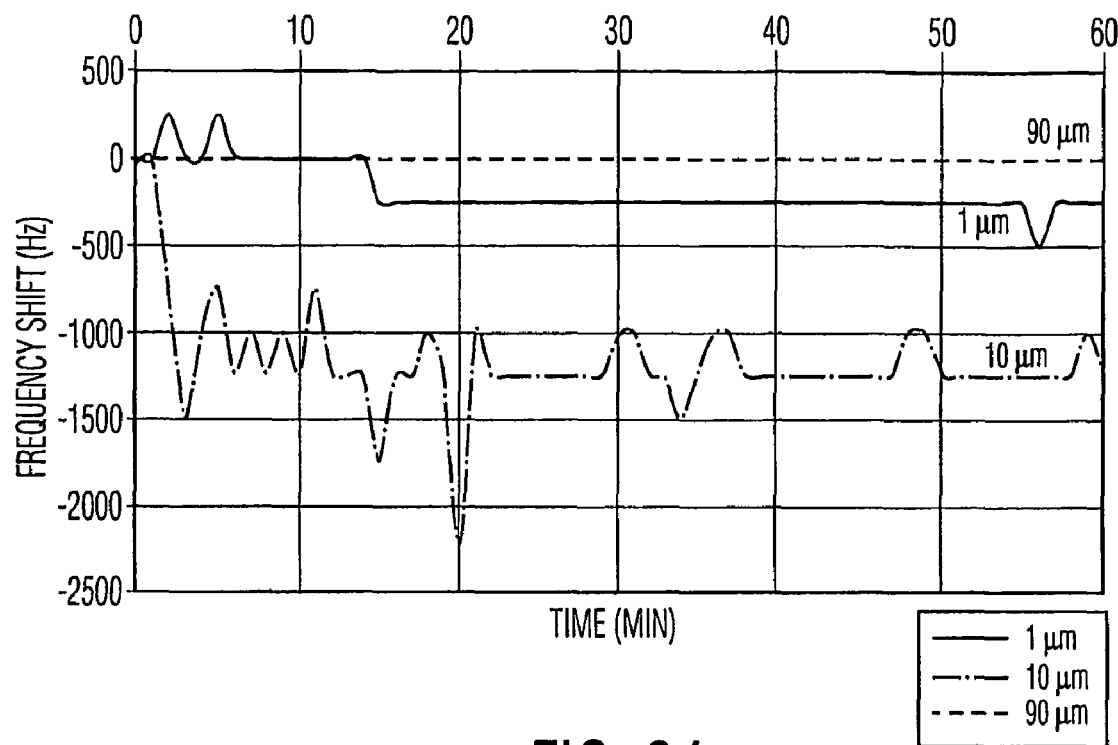
FIGS. 24a-24c show graphs of the change in MAIA resonant frequency as a function of time for the sedimentation and packing experiment measured at: (24a) 5 MHz, (24b) 15 MHz and (24c) 25 MHz at three different polystyrene sphere diameters.
Figure 24B:
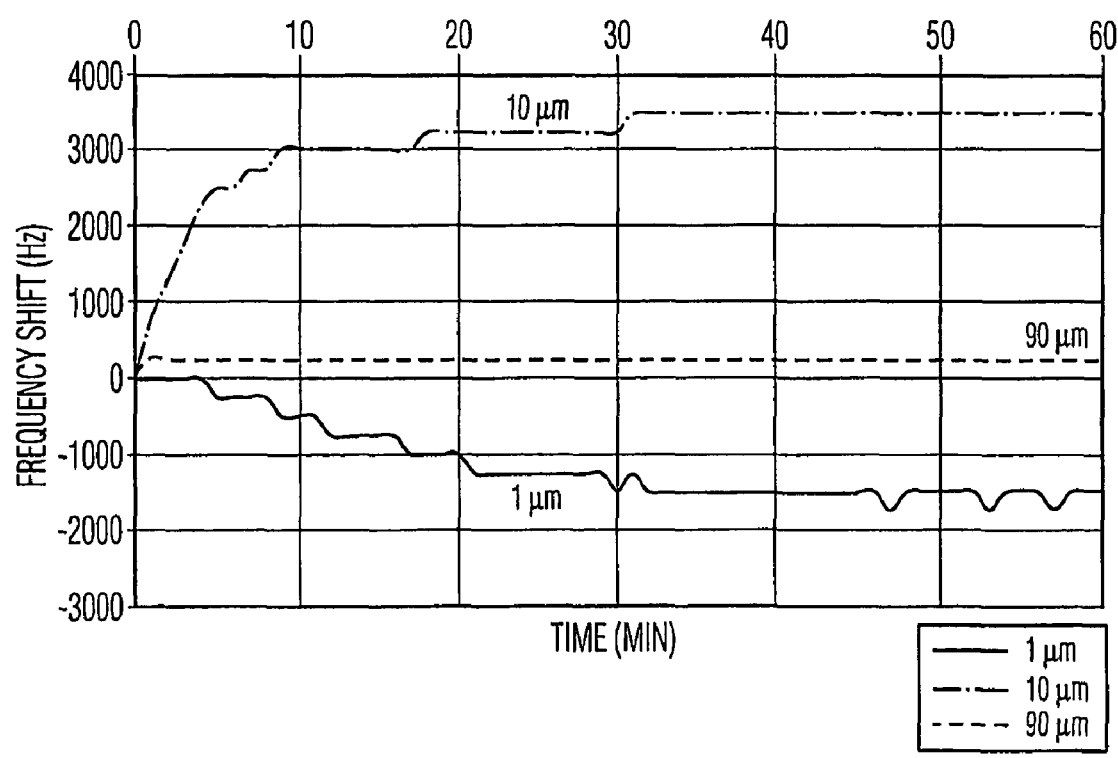
Figure 24C:
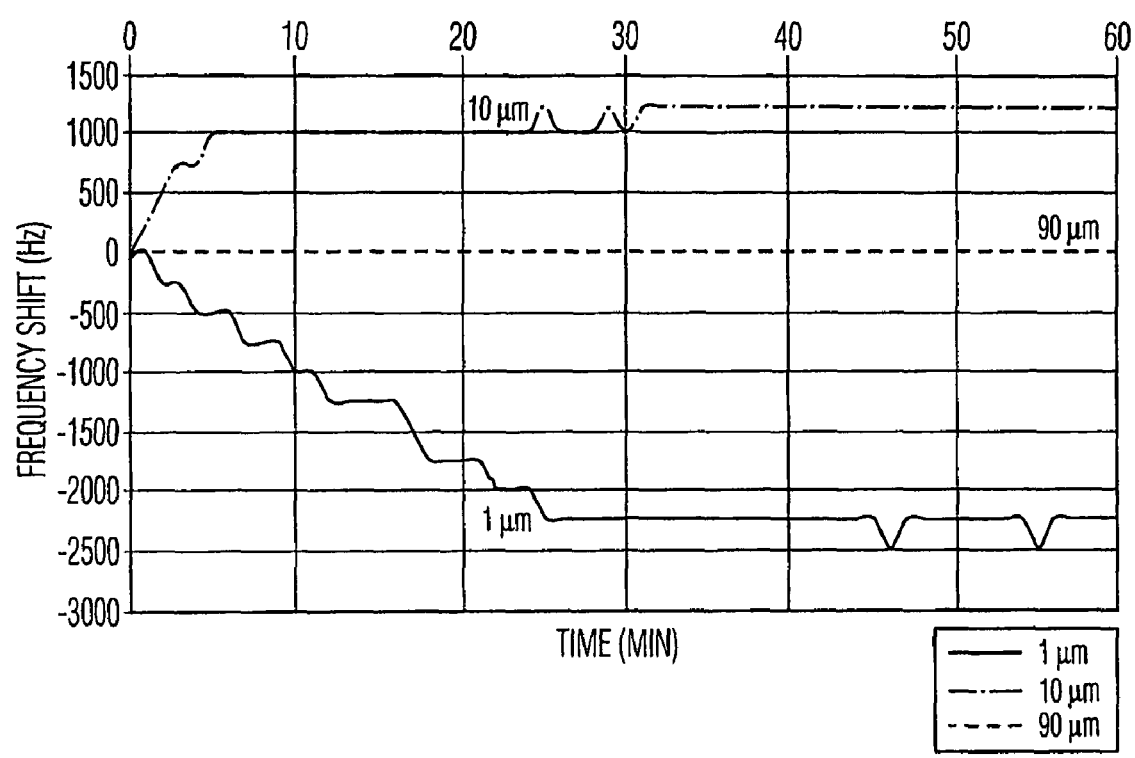
Figure 25A:
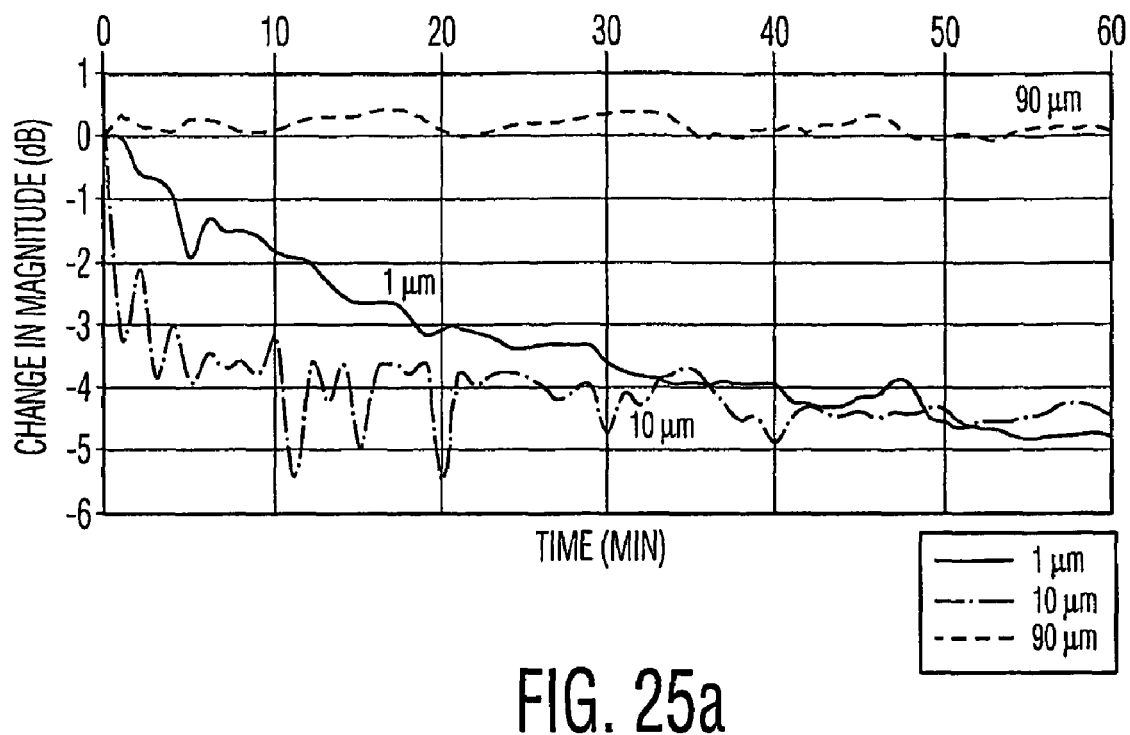
FIGS. 25a-25c show graphs of the change in MAIA resonant amplitude as a function of time for the sedimentation and packing experiment measured at: (25a) 5 MHz, (25b) 15 MHz and (25c) 25 MHz at three different polystyrene sphere diameters.
Figure 25B:
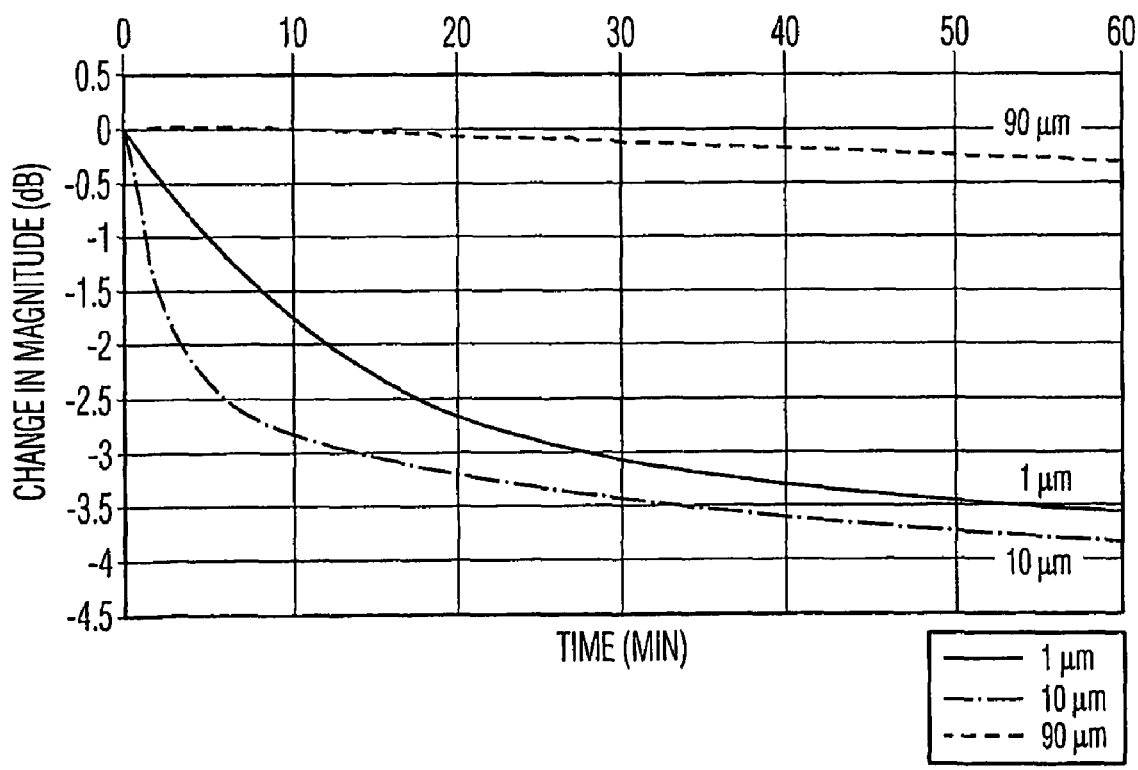
Figure 25C:
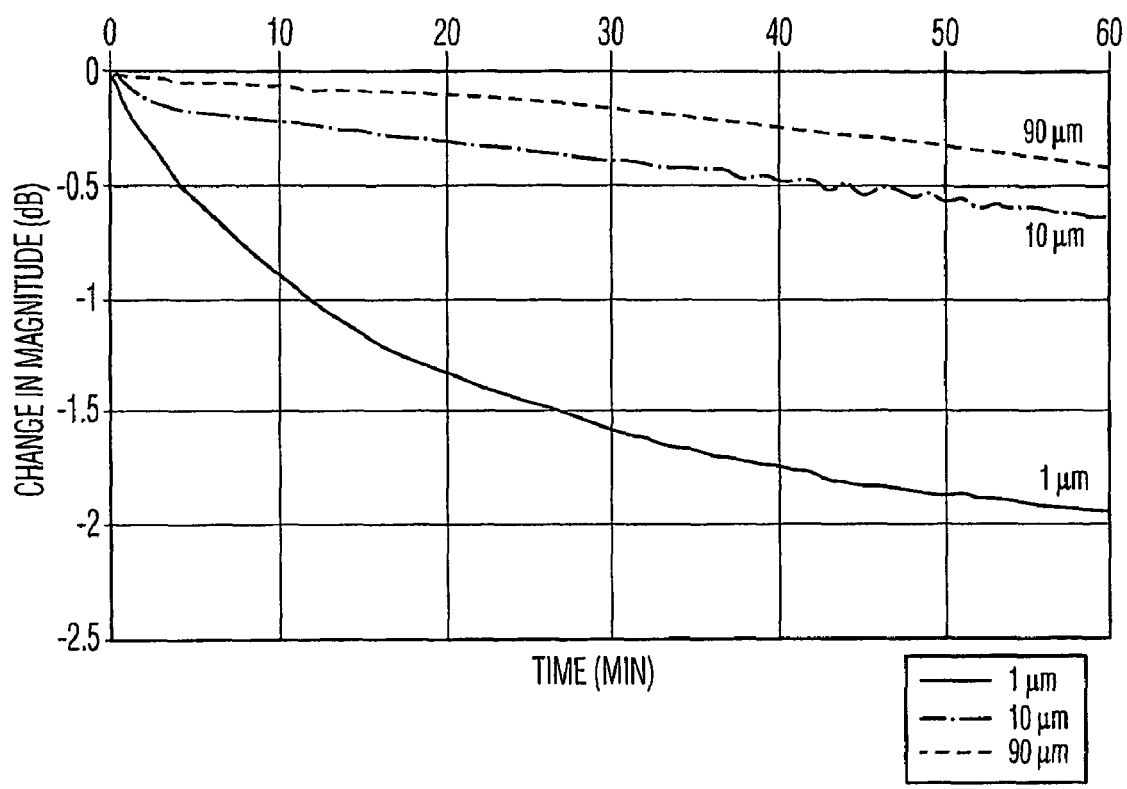

Similar experiments were conducted using the 90 μm polystyrene spheres. Contrary to the previous experiments, very small changes were observed. FIGS. 23 a-c shows the effects of the 90 μm polystyrene spheres sedimentation and packing has on the resonant frequency of a 5, 15 and 25 MHz. The small resonant frequency change with time is probably due to the small surface contact as depicted in FIG. 20c. Due to the large diameter of the 90 μm spheres, minimal contact is achieved between the surface of the crystal and the spheres. One needs to recall that the depth of penetration is in the order of tens-to-hundreds nanometers. Therefore, the contributions from all the spheres are not large enough to elicit a shift in resonant frequency or peak amplitude. However, one may notice an appearance of slight changes with increase of the frequency (as shown in FIG. 23c).

The results presented above described the behavior of the suspension at two discrete times, i.e. at the beginning and the end of the experiment. In the experiments the data was collected every minutes for one hour.

(v) Change in MAIA Resonant Frequency and Amplitude as a Function of Time

The results presented in FIGS. 24a-c and 25a-c provide an important insight on the formation process of an interfacial layer at the MAIA sensor surface. Accumulation of polystyrene spheres at the MAIA surface causes quite strong and distinct changes in the resonant frequency and amplitude of the sensor. In dilute suspensions the net downward velocity of particles (toward the sensor surface in the instant case) during the sedimentation process, in first approximation, depends on the diameter of the particles, the difference in density between the suspending fluid and the particles and the viscosity of the suspending fluid. In our case, these velocities are equal to $2.1 \times 10^{-6}$, $2.1 \times 10^{-4}$ and $1.7 \times 10^{-2}$ cm/sec for the 1, 10 and 90 micron particles respectively. For the polystyrene particles placed just in the top layer of the suspension column in the cell (the height of the column equal to 5 mm), the sedimentation time is about 60 hours, 37 minutes and 30 seconds for 1 micron, 10 microns and 90 microns spheres. However, for the particles positioned at the distance equal to their diameters from the MAIA surface, the sedimentation time is the same for all these three kinds of particles and is equal to 0.5 second. It should be understood that these values were calculated using a theoretical model for dilute suspension and therefore they only approximate the actual sedimentation times.

Also, it is important to remember that the MAIA averaging process depends on the penetration depth of the wave, i.e. on the frequency of the MAIA wave. As a result, the MAIA is sensitive to the increase of the number of spheres and the number of sphere layers only over the layer thickness equal to the penetration depth. At 5 MHz the depth of penetration is relatively large, therefore a large volume is monitored and the wave is rather sensitive to volume-controlled processes in contrast to 15 and 25 MHz waves which rather monitor interfacial effects. This feature is clearly seen when comparing the decay of the amplitude of the 5, 15 and 25 MHz for 1 micron spheres shown in FIGS. 25a-c. At 5 MHz, the decay is slow and linear, but at 15 and 25 MHz fast and exponential. Also, the amplitude decay is much more rapid for 10 micron then for 1 micron spheres. From the presented graphs it results that each frequency provides a distinct signature of the MAIA response, which is an advantageous feature of this proposed application of piezoelectric sensor technology.

Therefore, the use of piezoelectric shear wave sensor technology for the characterization of nonuniform liquid media such as suspensions is demonstrated above. In particular, various processes at the boundary between suspensions and various solid surfaces can be studied with MAIA sensors. The MAIA sensor can be applied for monitoring a broad range of phenomena taking place at the interface of the suspension and the MAIA sensor. The suspensions in the example consisted of polystyrene spheres of 3 different diameters suspended in a buffer (DMEM). The MAIA sensor operated at its fundamental frequency of 5 MHz and two harmonic frequencies of 15 and 25 MHz. The sensor was capable of monitoring the sedimentation and solid phase accumulation processes at the MAIA sensor surface. These processes involved changes in interfacial density, stiffness and viscosity. Also, the piezoelectric interfacial sensor could differentiate between different sizes of spheres in suspension. As a result this method can be used for the development of a particle size distribution sensor. In addition, the MAIA sensor provided means for producing a resonant type interaction with suspension particles. This resonant interaction can be used for measuring bonding energy of a suspended particle to the surface.

The MAIA sensor, operating at different frequencies, is capable of "slicing" and probing the media at different depths, hence it can reveal different interfacial phenomena, including interfacial structural arrangement. The sensor exhibits high sensitivity, reproducibility and stability.

Example 4

Interaction of Solid Particles with Various Surfaces Using MAIA Sensors

In an exemplary embodiment, a MAIA sensor can be used to identify properties of a particle or particles coupled to the sensor surface. In this example, the case of weak coupling condition is explored. A mechanical model is presented and formulas of motion are provided based on the analysis of the interaction forces.

Figure 26:
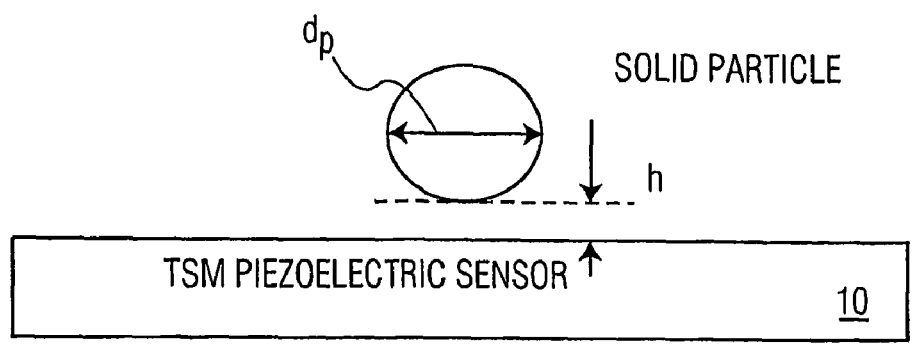
FIG. 26 shows a diagram of a solid particle interacting with an MAIA sensor in air.
Figure 27:
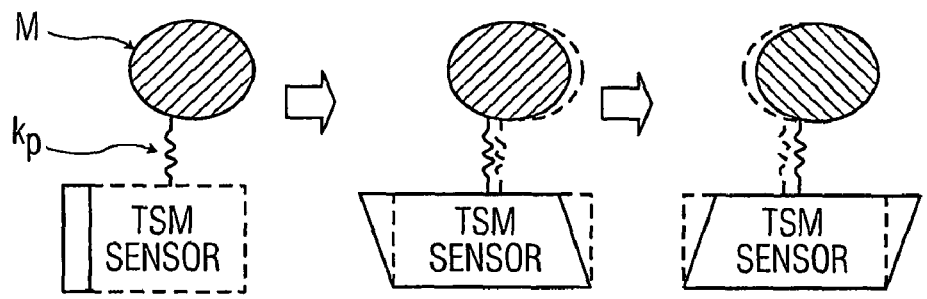
FIG. 27 shows a diagram of shear motions of a solid particle coupled with an MAIA sensor.

(i.) Interaction Forces Between a Solid Particle and the Surface of a MAIA Sensor This example focuses on the interaction of a solid particle P in contact with a MAIA sensor 10 in air. A solid particle when placed on a solid surface, in general, is not in a direct contact with the surface, but is separated from it by a short distance h, as shown in FIG. 26. FIG. 27 shows the shear motions of the surface of a MAIA sensor coupled with a solid particle.

The interaction forces between a solid particle P and the surface of a MAIA sensor 10 come from various sources, such as Van der Waals force, friction force, electrostatic force, capillary force and gravitational force, etc.

(a) Van der Waals Force

Van der Waals free energy, $W_{vdw}(h)$, and Van der Waals (VDW) force, $F_{vdwh}(h)$ for a solid particle with the size of tens of nanometers to several hundred micrometers, in contact with a surface can be described by:

$$W_{vdw}(h) = -\frac{A \cdot d_p}{12 \cdot h} \text{ and } F_{vdw}(h) = \frac{A \cdot d_p}{12 \cdot h^2} \quad \text{(Eq. 10)}$$

where, h, is the distance between the particle and the sensor surface; A, is Hamaker constant about $(0.4~4) \times 10^{-19}$ J; $d_p$, is the diameter of a particle (by assuming the particle is spherical).

Figure 28:
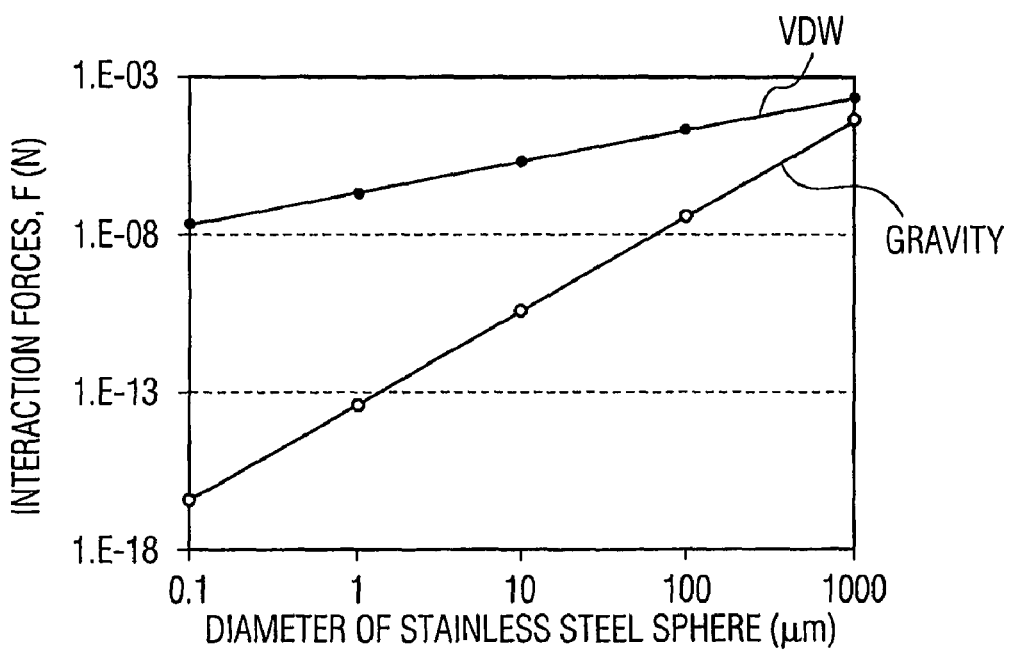
FIG. 28 shows a graph comparing Van der Waals force and gravity force.

By comparing the VDW force between the particle and the surface of a MAIA sensor with the gravity force of the particle, it is shown in FIG. 28 that the VDW force becomes several orders greater than the gravity force for a nano/micro particle. For example, the VDW force between a particle and a surface is about $10^7$ times larger than the gravity force for a stainless steel bead of 1 μm diameter.

(b). Other Forces

Other interaction forces, such as electrostatic force, friction force, capillary force, etc., play a less important role than the VDW force in the interfacial interaction of a solid particle with the gold surface (electrode) 11 of a MAIA sensor 11 in air. Under certain conditions, such as proper grounding and discharging of the particle P and the sensor 10, smooth surface of the sensor, low humidity in the air, etc., the Van der Waals force can be considered as the dominant interaction between a solid particle P and the MAIA sensor 10.

(c) Coupling Coefficient between a Solid Particle and the Surface of a MAIA Sensor The coupling coefficient, $k_p$, represents the coupling strength of the interaction between a solid particle P and a MAIA sensor 10. By knowing the Van der Waals force, $F_{vdw}$ (d), the coupling coefficient, $k_p$, can be estimated by $$k_p = -\frac{\partial(F_{vdw})}{\partial h} = \frac{A \cdot d_p}{6 \cdot h^3} \quad \text{(Eq. 11)}$$

Figure 29:
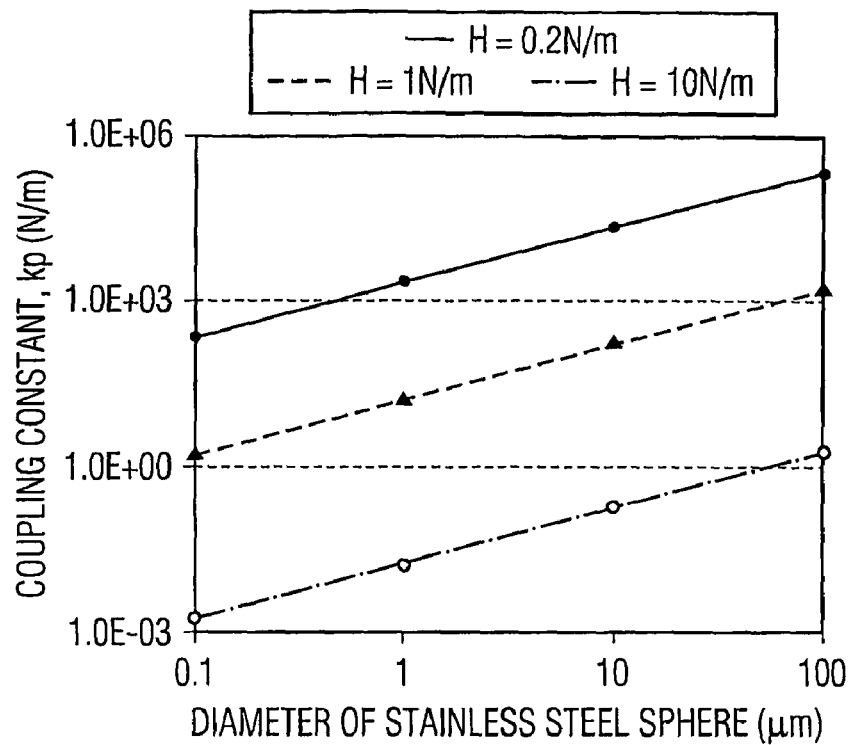
FIG. 29 shows a graph of coupling coefficient, $k_p$, as a function of the diameter of a solid particle with different distance, h, between the particle and the surface.

FIG. 29 shows the dependence of the coupling strength, $k_p$, on the diameter, $d_p$, of the particle. The coupling coefficient, $k_p$, is linearly proportional to the diameter of a particle but inversely proportional to the cube of the distance, h, between the particle P and the surface of a MAIA sensor 10.

For a particle of 1 μm diameter in contact (h=0.2 nm, solid line in FIG. 29) with the surface of a MAIA sensor, the coupling strength, $k_p$, is about $10^3$ N/m.

By obtaining the values of Van der Waals force or the coupling coefficient from the MAIA sensor measurements, and given the type of material, the diameter, or the mass of the micro-particle can be determined. This allows the MAIA sensor to operate as a nano-particle monitor in the research and manufacture of nano-scale mechanical and micro-electro-mechanical (AEM) devices.

(d) Resonant Frequency of a Solid Particle Coupled with a MAIA Sensor

In the practical measurements of the interaction properties using MAIA sensor technique, it is actually the change of frequency or phase from the original characteristic of the sensor caused by the interaction of particles with the sensor surface that is being measured. Then, other parameters, such as mass, size and type, are derived from the measurement results. When the resonant frequency of the coupled particle is close to the resonant frequency of a MAIA sensor, then the two resonators are coupled, and the sensitivity of the MAIA to the presence of the particle increases. The resonant frequency of the particle, $f_p$, is related to the diameter of the particle, $d_p$, by $$f_p = \frac{1}{2\pi}\sqrt{\frac{k_p}{m_p}} = \frac{1}{2\pi}\sqrt{\frac{A}{\pi \cdot h^3 \cdot d_p^2 \cdot \rho_p}} \qquad \text{(Eq. 12)}$$

where, $\rho_p$, mass density of a particle.

Figure 30:
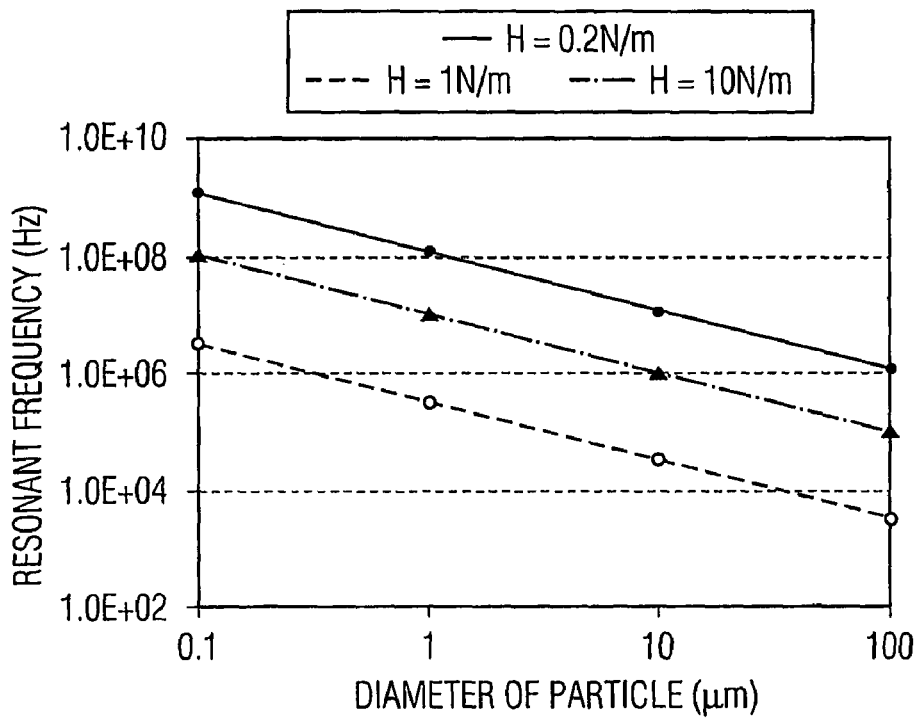
FIG. 30 shows a graph of the resonance frequency of a solid particle coupled with a MAIA sensor at different heights, h, of the particle above the surface.

FIG. 30 shows that the resonant frequency of a particle $f_p$ is inversely proportional to the particle's radius, R. When $f_p$ approaches the fundamental resonant frequency of a MAIA sensor, $f_s$, the coupling enters into resonance and has maximum energy transfer.

Since a MAIA sensor usually has a resonant frequency, $f_s$, in the range of 1 MHz ~100 MHz, strong coupling is expected when $f_p$, is close to $f_s$.

It can be seen in FIG. 30 that $f_p$ is between 1 MHz and 100 MHz when the diameter of a particle is between 1 um and 100 um (h≈10.2 nm, for a particle placed on a surface), which suggests that MAIA sensors are capable of detecting solid particles with diameters from 1 um to 100 um.

Figure 31:
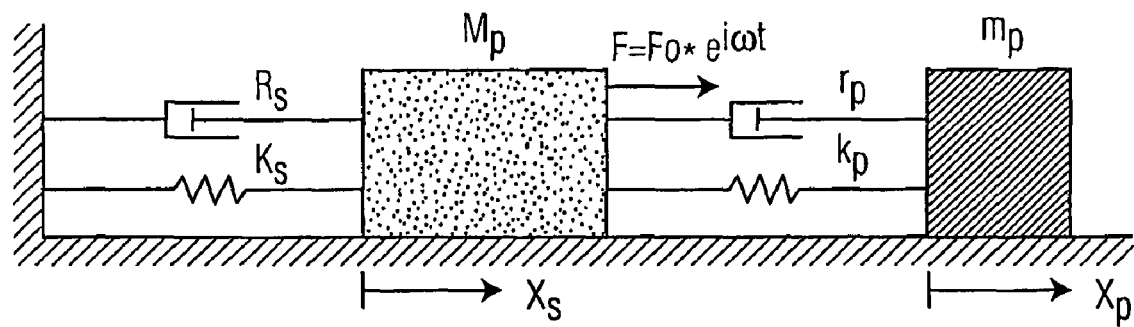
FIG. 31 shows a diagram of a mechanical model of an interaction between a solid particle and the surface of a MAIA sensor.

(d) Mechanical Model of an Interaction between a Solid Particle and the Surface of a MAIA Sensor A proposed mechanical model describing the interaction of a solid particle with the surface of a MAIA sensor is shown in FIG. 31.

A piezoelectric MAIA sensor is represented by a mechanical resonator consisting of $M_s$, $K_s$ and $R_s$; $M_s$, is the mass of the MAIA sensor, $$M_s = \frac{\pi \cdot d_s^2}{4} \cdot t_s \cdot \rho_s,$$

and, $K_s$, is the elasticity of the sensor, $$K_s = \frac{\pi^3 \cdot d_s^2 \cdot c_s}{4 \cdot t_s},$$

where $d_s$, $t_s$, $\rho_s$ and $c_s$ are the diameter, thickness, density and elastic constant of the sensor, respectively; $x_s$, and $x_p$, are the displacements of the surface of a MAIA sensor and the coupled particle, respectively; $R_s$, is due to the energy loss. Since a quartz crystal resonator has a very high quality factor, Q, $R_s$ is usually very small. The fundamental resonance feature frequency of the MAIA sensor, $f_s$, is given as $$f_s = \frac{1}{2\pi} \cdot \sqrt{\frac{K_s}{M_s}} \qquad \text{(Eq. 13)}$$

The mass, $M_s$, is driven by a force $F=F_o*e^{j\omega t}$, which is equivalent to an electrical voltage to generate the shear motion of a MAIA sensor. The coupled particle is modeled as a rigid mass, $m_p$. The interfacial interaction between the particle and the surface of a MAIA sensor is represented by a spring, $k_p$, and a dashpot, $r_p$.

The equations of motion based on the mechanical model can be written as Equations (14) and (15), $$M_s \cdot \ddot{x}_s + R_s \cdot \dot{x}_s - r_p \cdot (\dot{x}_p - \dot{x}_s) + K_s \cdot x_s - k_p \cdot (x_p - x_s) = F_o \cdot e^{j\omega t} \qquad (14)$$

$$m_p \cdot \ddot{x}_p + r_p \cdot (\dot{x}_p - \dot{x}_s) + k_p \cdot (x_p - x_s) = 0 \qquad (15)$$

where, $R_s$, is the damping factor in the motion of the MAIA sensor; $r_p$, is the damping factor due to the coupling between the MAIA sensor and the particle.

A MAIA sensor has a very high quality factor, Q, of over $10^6$. Thus the loss in the operation of the mechanical oscillation (the oscillation of MAIA sensors, related to the value of $R_s$) can be ignored in most consideration. The energy loss during the coupling mostly comes from the friction force between the particle and the sensor surface. To get a preliminary outlook of the interaction between the particle and the surface in this example, the loss r during the coupling is neglected.

Under the assumption of lossless conditions, $R_s = r_p = 0$, the equations of motion can be simplified as $$M_s \cdot \ddot{x}_s + K_s \cdot x_s - k_p \cdot (x_p - x_s) = Fo \cdot e^{j\omega t} \qquad (16)$$

$$m_p \cdot \ddot{x}_p k_p \cdot (x_p - x_s) = 0 \qquad \text{(Eq. 17)}$$

Assume that the displacements, $x_s$ and $x_p$, are in the forms of $$x_s = A_s \cdot e^{j\omega t} \text{ and } x_p = A_p \cdot e^{j\omega t} \qquad \text{(Eq. 18)}$$

The amplitudes of the displacements, $A_s$ and $A_p$, can be written as $$\frac{A_s}{\frac{F_o}{K_s}} = \frac{1 - \frac{\omega^2}{\omega_p^2}}{\left(1 - \frac{\omega^2}{\omega_p^2}\right) \cdot \left(1 + \frac{k_p}{K_s} - \frac{\omega^2}{\omega_s^2}\right) - \frac{k_p}{K_s}} \qquad \text{(Eq. 19)}$$

and $$\frac{A_p}{\frac{F_o}{K_s}} = \frac{1}{\left(1 - \frac{\omega^2}{\omega_p^2}\right) \cdot \left(1 + \frac{k_p}{K_s} - \frac{\omega^2}{\omega_s^2}\right) - \frac{k_p}{K_s}} \qquad \text{(Eq. 20)}$$

where $\omega_s = \sqrt{\frac{K_s}{M_s}}$ and $\omega_p = \sqrt{\frac{k_p}{m_p}}$ are the resonant frequencies of a MAIA sensor and a particle, respectively.

(e) Resonance Frequency of a MAIA Sensor Coupled with a Solid Particle

A MAIA sensor loaded with a solid particle can be considered as a coupling mechanical system as it is depicted in FIG. 31. The resonant frequency of this coupling system, $\omega_c$, is different from the fundamental resonant frequency of a unloaded MAIA sensor, $\omega_s$. The relation between $\omega_c$ and $\omega_s$ can be found when the determinant in the right side of (10) becomes zero or the amplitude, $A_s$, becomes infinity.

$$\left(1-\frac{\omega^2}{\omega_p^2}\right)\cdot\left(1+\frac{k_p}{K_s}-\frac{\omega^2}{\omega_s^2}\right)-\frac{k_p}{K_s}=0 \quad\text{(Eq. 21)}$$

the solution to this equation gives the resonant frequency of the coupling system, $\omega_c$, is derived as $$\omega_{c1,2}= \left(\frac{1}{2}\cdot\left[\left(\frac{k_p}{m}+\frac{K_s}{M}+\frac{k_p}{M}\right)\pm\sqrt{\left(\frac{k_p}{m}+\frac{K_s}{M}+\frac{k_p}{M}\right)^2-4\cdot\frac{k_p}{m}\cdot\frac{K_s}{M}}\right]\right)^{1/2} \quad\text{(Eq. 22)}$$

It shows that the resonant frequency of the coupling system, $f_c=\omega_c/2\pi$, is a function of the masses of the MAIA sensor, M, and the coupled object, m, as well as the spring coefficients, $K_s$ and $k_p$. If the properties of a MAIA sensor, M and $K_s$, are given, then by knowing the mass, m, of the loaded particle, the coupling coefficient, $k_p$, can be determined from the measurements of the resonant frequency, $\omega_c$, of the coupling system. This is very useful in measuring the properties of the interactions between different particles and the surface.

Figure 32:
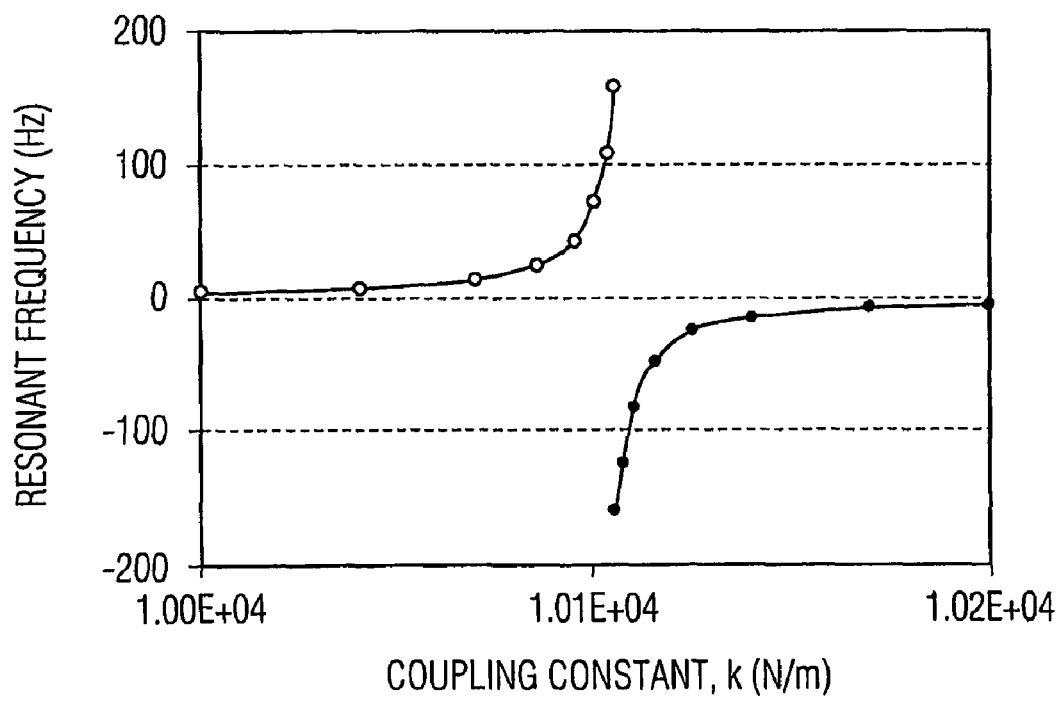
FIG. 32 shows a graph depicting the relative change in the resonant frequency, $\Delta f_c/f_s$, vs. coupling constant, $k_p$.

FIG. 32 shows the dependence of the relative change in the resonant frequency, $\Delta f_c/f_s$, on the coupling coefficient, $k_p$, for a MAIA sensor loaded with a stainless steel sphere (about 10 µm diameter with mass, m). The MAIA sensor has a fundamental resonant frequency, $f_s=5$ MHz. $\Delta f_c=f_c-f_s$, is the change in the resonant frequency of the MAIA sensor due to the particle loading.

One can find that there is a special value for the coupling coefficient, $k_p$, defined as the critical coupling coefficient:

$$k_{pc}=m_p\cdot\frac{K_s}{M_s}=m_p\cdot\omega_s^2=m_p\cdot(2\pi f_s)^2 \quad\text{(Eq. 23)}$$

This happens when the natural frequency of a particle, $f_p$, is equal to the fundamental frequency of a MAIA sensor, $f_f$. At that condition, the maximum frequency change in the resonance feature frequency is observed, i.e. for a 5 MHz MAIA sensor with a 10 um gold sphere placed on its surface, the maximum frequency change is about 158 ppm or 800 Hz.

When $k_p$ is larger than $k_{pc}$, the resonant frequency of the coupling system, $f_{c2}$, is less than the resonant frequency of a unloaded MAIA sensor, $f_s$. This actually corresponds to the case of mass loading on a MAIA sensor, where a decrease in the resonant frequency, $\Delta f_{c2}=f_{c2}-f_s<0$, is measured. This comes from a strong coupling between the loaded object and the MAIA sensor.

If $k_p$ is smaller than $k_c$, the resonant frequency of the coupling system, $f_{c1}$, is greater than $f_s$. A weak coupling between the loaded object and the MAIA sensor happens and an increase in the resonant frequency, $\Delta f_{c1}=f_{c1}-f_s>0$, is predicted.

Figure 33:
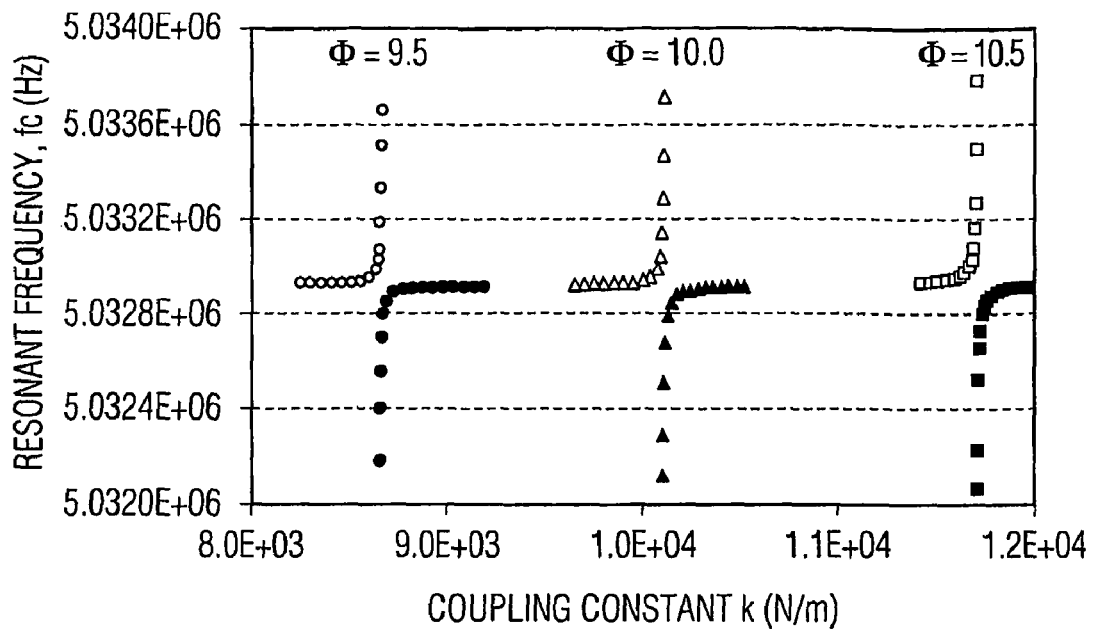
FIG. 33 shows a graph depicting resonant frequencies of the coupling system, $f_c$, vs. the coupling constants $k_p$, for particles with different diameters.

In FIG. 33 the dependence of the resonance frequency of the coupling system, $f_c$, on the coupling coefficient, $k_p$, is plotted for particles with different diameters. It is clear in FIG. 33 that a small change of about 5% in the diameter or 15% in the mass of a sphere could significantly change the critical coupling coefficient for a particle and makes it hard for the same MAIA sensor to detect all of the three sizes of particles shown in FIG. 33. This can be considered as an advantage because the MAIA sensor has a high selectivity but at the expense of limited detection range.

Figure 34:
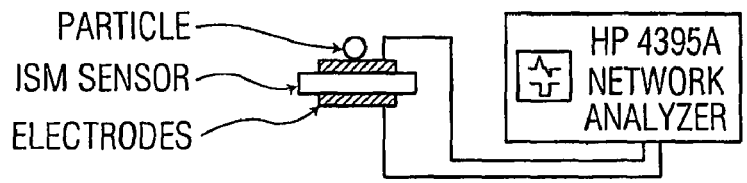
FIG. 34 shows a diagram of an HP 4395A Network Analyzer measurement system for monitoring the interaction of solid particles with a MAIA sensor.

Experiments have been designed to study the interaction between solid particles and the MAIA sensor surfaces. An HP 4395A Network Analyzer measuring system is shown in FIG. 34. The MAIA scattering parameter $S_{21}$ is measured as a function of various particle loading conditions. The changes in the resonance frequency, amplitude and phase due to the particle loading can be accurately determined.

Figure 35:
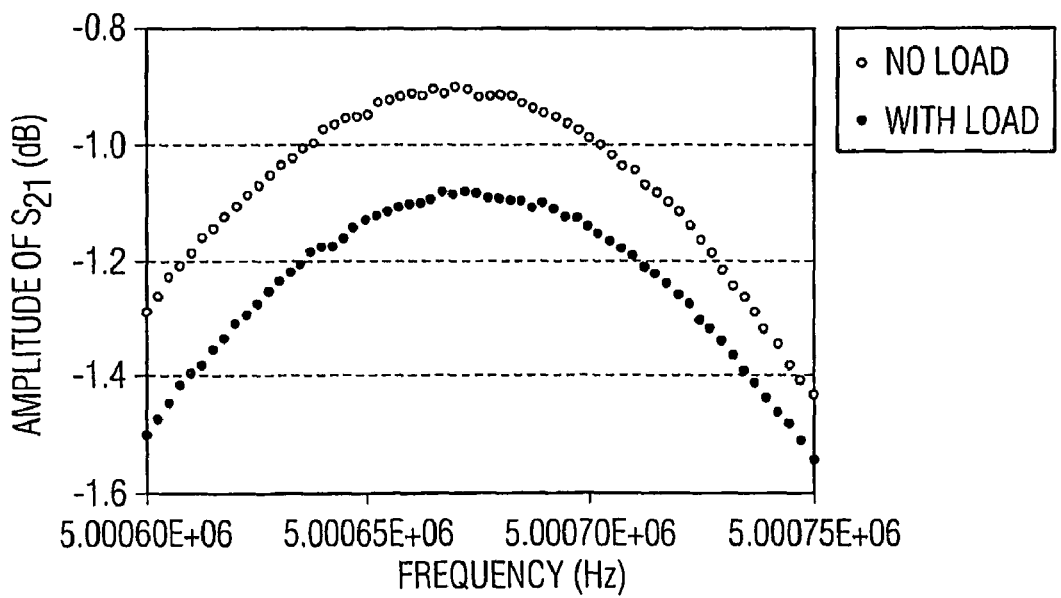
FIG. 35 shows a graph of the amplitude of $S_{21}$ for a 5 MHz MAIA sensor with no load and loaded with two stainless steel spheres (30 µm in diameter), as a function of the frequency.

FIG. 35 shows the frequency response of the amplitude of the reflection coefficient, $S_{21}$, for a 5 MHz MAIA sensor loaded with two 30 um spheres made of stainless steel Type 316 (austenitic, from Duke Scientific Corporation). The resonant frequency of the MAIA sensor is increased by 3 Hz with the particle loading. This is in contrast to a typical mass loading effect, caused by thin solid film and mass loading caused by liquid loading, where the resonant frequency decreases.

The change of the resonant frequency, $\Delta f_c=f_c-f_s$, is 3 Hz, or $\Delta f_c/f_s$ is about 0.6 ppm. Based on the mechanical model presented above (see Eq. 23), this corresponds to an interfacial coupling coefficient, $k_p$, of $1.08\times10^4$ N/m.

As discussed above, a relatively large frequency change due to a particle loading only happens when the resonant frequency of a particle is close to the fundamental frequency of a MAIA sensor. Thus, for a MAIA sensor, with the given resonance feature frequency, the effective interaction takes place only for the particles within a well defined range of diameters, since the interaction constant has a fixed value. Since the diameter of the particle can be changed in the experiment, one may observe only the given resonance frequency change. However, if one designs an experiment in which the interaction constant between the particle and the sensor surface can be controlled, then the change in the resonance frequency of the interaction can by directly observed. In the case of stainless steel particles, the interaction constant can be controlled by an external magnetic field.

Figure 36:
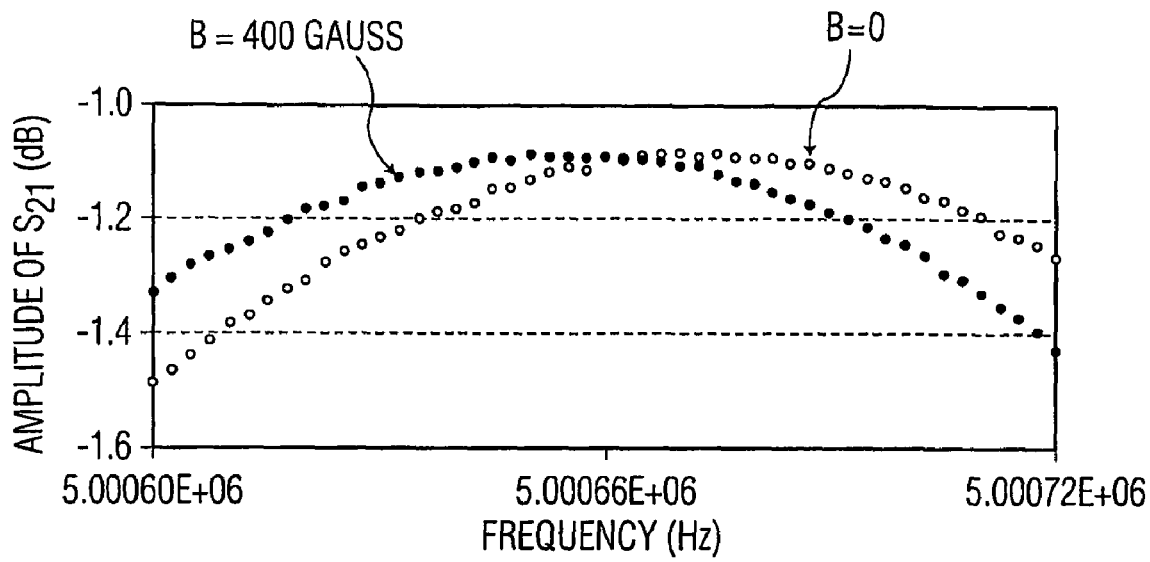
FIG. 36 shows a graph of the MAIA $S_{21}$ loaded with a stainless steel particle under an external magnetic field, as a function of frequency.

FIG. 36 shows the different frequency responses of the amplitude of the reflection coefficient, $S_{21}$, for a MAIA sensor loaded with two stainless steel spheres with and without a magnetic field (B=400 Gauss). It can be seen that the resonant frequency shift is about 12.5 Hz, much larger than the 3 Hz change measured without magnetic field. The resonance frequency of the MAIA sensor decreases. This suggests that the interaction constant increases since the magnetic field decreases the distance between the particle and the surface.

Figure 37:
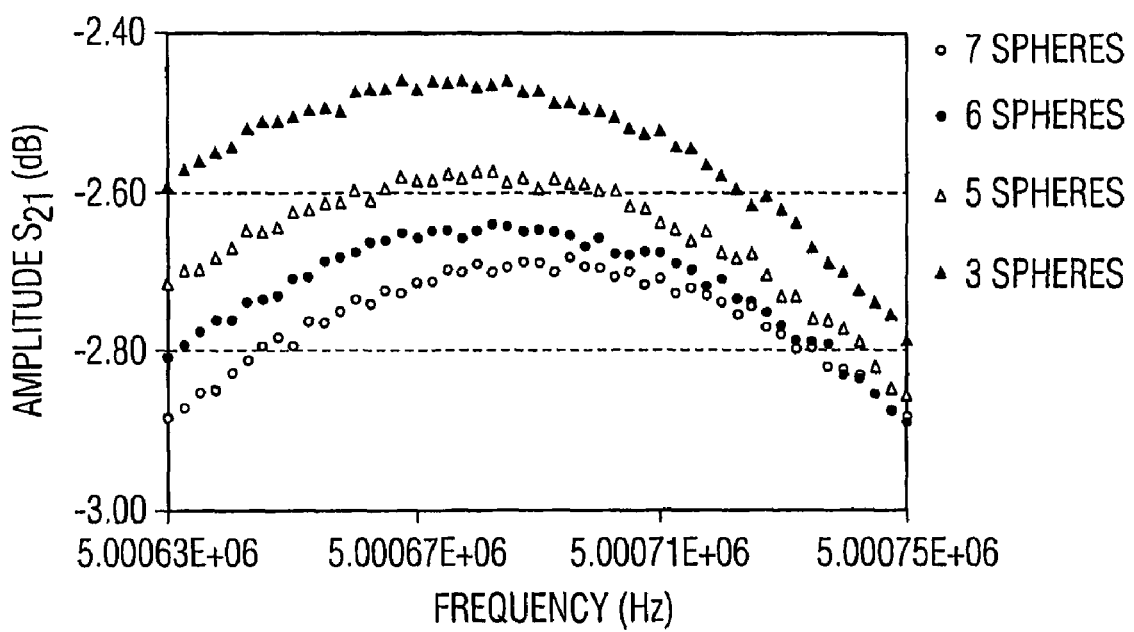
FIG. 37 shows a graph of the frequency response of the amplitude of $S_{21}$ loaded with stainless steel spheres under a magnetic field.

FIG. 37 shows the responses of a MAIA sensor to removals of particles under magnetic field. A 5 MHz MAIA sensor was loaded with seven stainless steel spheres with sizes of 30 µm. After a magnetic field (B=400 Gauss) was applied, a single sphere was removed successively except the last step where two spheres were removed. An average frequency shift of 5 Hz was observed for the removal of a single sphere and 10 Hz for the removal of two spheres. The results suggest that the interaction effect is linear and that particles do not interact between themselves.

Figure 38:
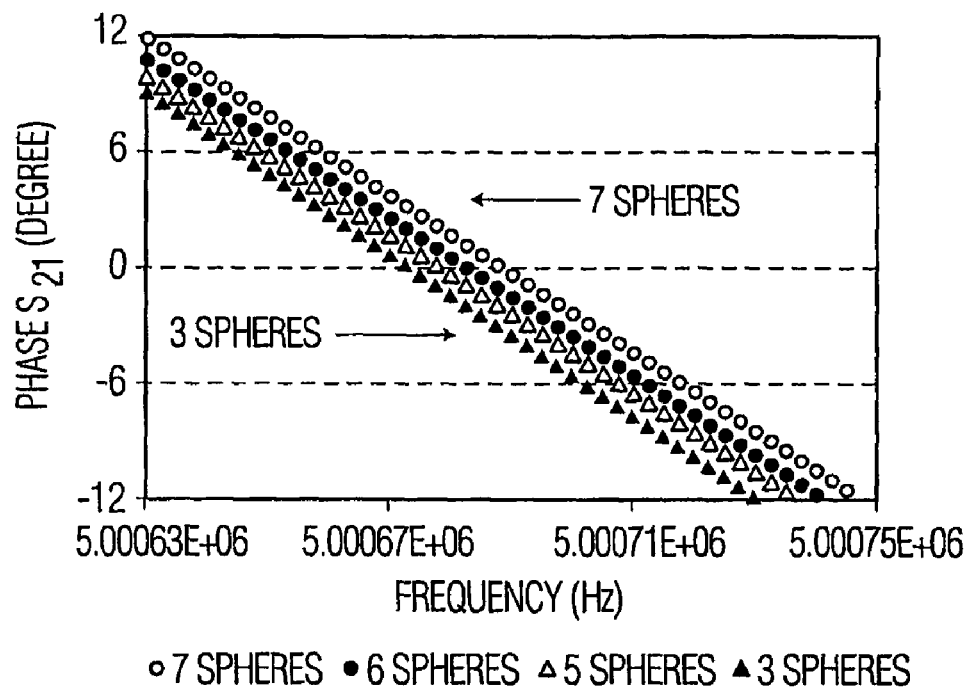
FIG. 38 shows a graph of the frequency response of the phase of $S_{21}$ loaded with stainless steel spheres under a magnetic field.
Figure 39:
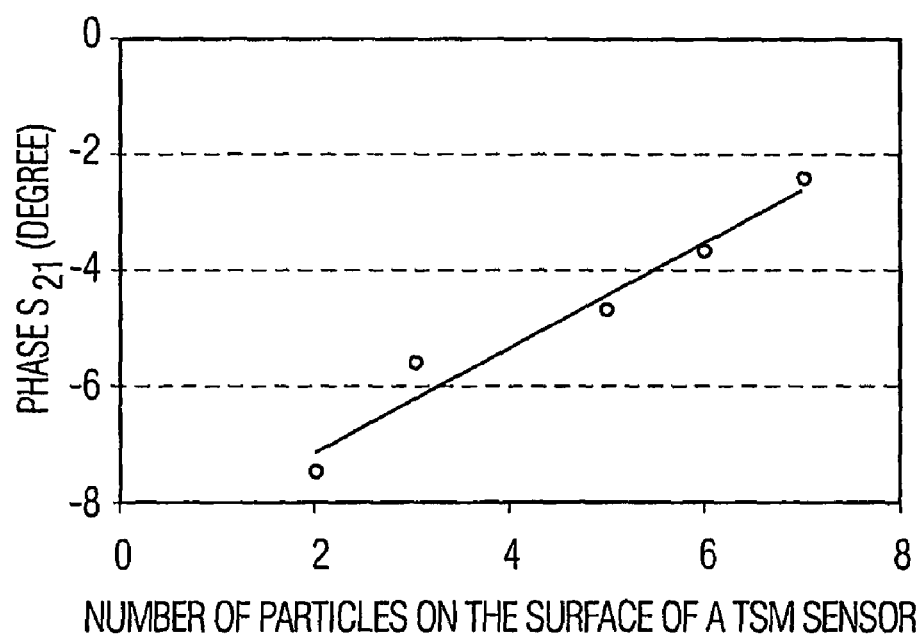
FIG. 39 shows a graph depicting the phase of $S_{21}$ vs. the number of particles on the surface of an MAIA sensor.

FIG. 38 is the corresponding frequency response of the phase of $S_{21}$. The phase at a certain frequency decreases with the decrease in the number of particles loaded on the MAIA sensor surface. It is seen more clearly in FIG. 39 that the phase changes as the number of particles on the sensor varies. The phase with no particle loaded is not zero due to the phase shift caused by the applied magnetic field. The obtained results suggest that the MAIA technique may be very useful for the study of various interfacial processes involving different particles and broad range of ambient conditions.

The natural frequency of the loaded particles depends on the properties of the particle and the interaction with the sensor. To obtain high resolution and sensitivity, the resonant frequency of MAIA sensor should be close to the natural frequency of the particle. Since the present, single plate, MAIA sensor has fixed resonant frequency, a sensor array integrated of MAIA sensors with various resonant frequencies is also desirable.

Figure 40:
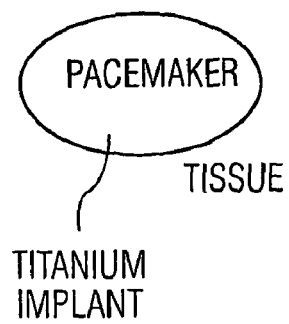
FIG. 40 shows a diagram of a pacemaker including an MAIA sensor.

FIG. 40 shows a diagram of a pacemaker 40 implanted within tissue 41. The MAIA sensor can be used with a pacemaker implant in order to determine that the pacemaker is functioning correctly, by measuring mechanical changes, such as elasticity associated with proper operation. Alternatively, the sensor can be used to determine that the body is not rejecting the pacemaker by measuring one or more of density and elasticity to determine fluid build-up, consistent with rejection. The MAIA sensor can be integrated within the structure of the pacemaker itself, or be placed in a location near the implant.

Figure 41:
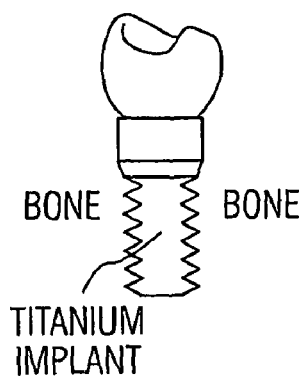
FIG. 41 shows a diagram of a tooth implant including an MAIA sensor.

FIG. 41 shows a diagram of a tooth implant 50. The MAIA sensor can be used with a tooth implant in order to determine that the tooth implant is not being rejected, or that it is not subject to infection, etc. The MAIA sensor can be placed within the structure of the implant or placed in a location near the implant.

Figure 42:
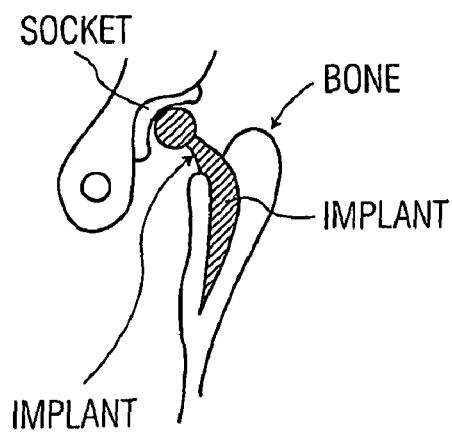
FIG. 42 shows a diagram of a hip implant including an MAIA sensor.

FIG. 42 shows a diagram of a hip implant 60. The MAIA sensor can be used with a hip implant in order to determine that the hip implant is not being rejected, or that it is not subject to infection, etc. The MAIA sensor can be placed at the location of the implant, or be integrated into the structure of the implant.

Figure 1A:
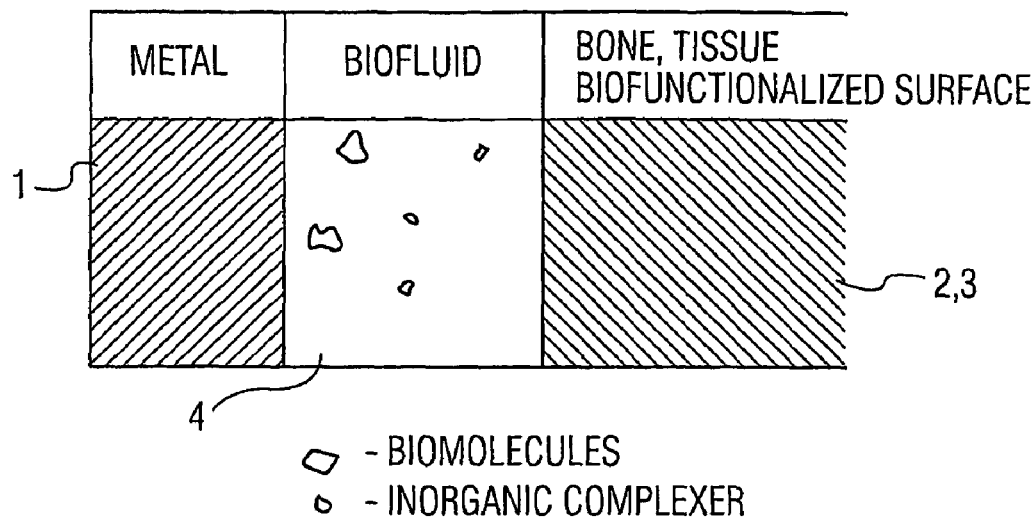
FIG. 1a shows a sectional view of an interaction between a titanium implant, bio-fluid, and bone.

Referring again to FIG. 1a, a diagram of layers is shown on a micrometer scale that the sensor can detect. Interactions detectable on this scale include the interaction at the bio-fluid, metal, bone, tissue, and bio-functionalized surfaces. Analysis of these layers or regions of the interfacial area can provide information about the interaction of an implant with adjacent bone and tissue.

Figure 1B:
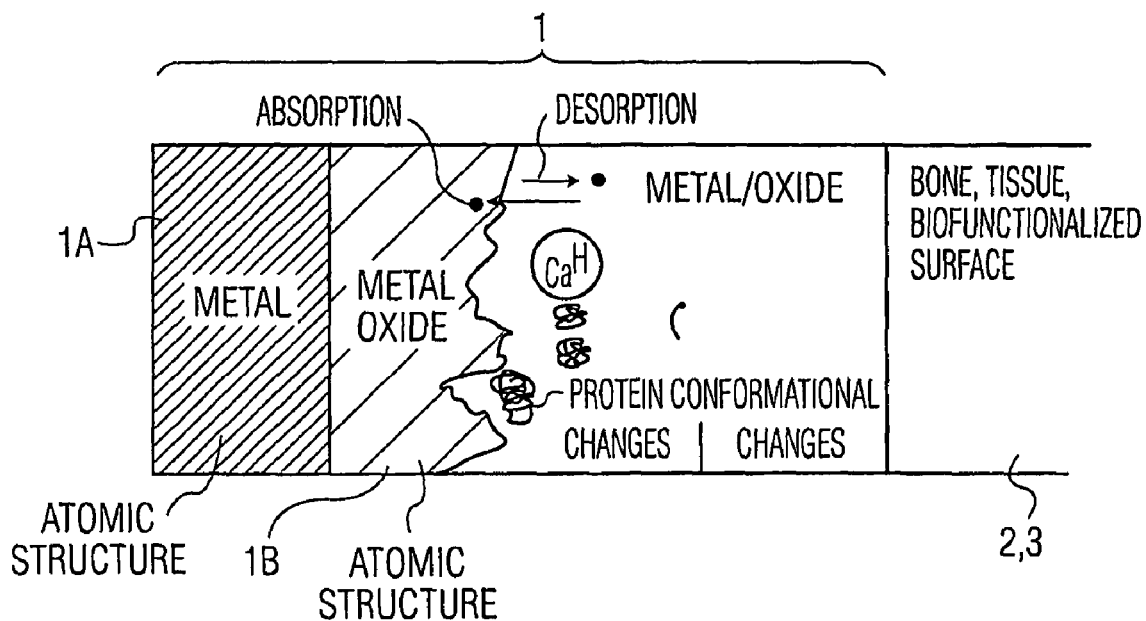
FIG. 1b shows a magnified sectional view of the interaction of FIG. 1.

Referring again to FIG. 1b, a diagram of layers or regions of an interfacial area are shown on a nanometer scale. Interactions detectable on this scale include the absorption of metal oxide, the interaction with water molecules and protein conformational changes. Detecting the presence of proteins and their changes can be used to derive functional meaning in analyzing the effectiveness of the hip implant.

Example 4

In Vitro Biochemical Detection

Figure 43:
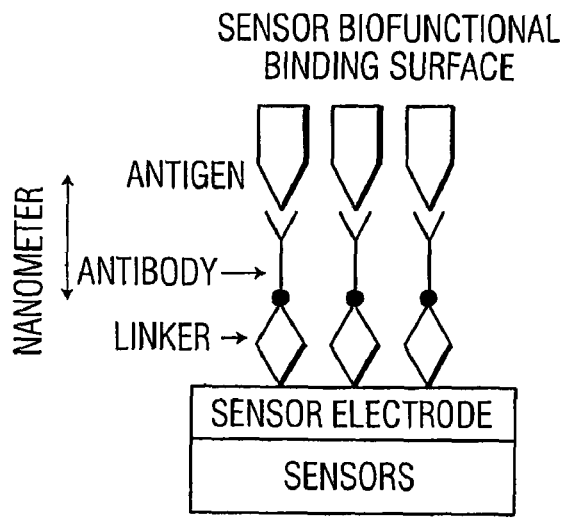
FIG. 43 shows a diagram of an MAIA sensor with a biofunctionalized binding surface
Figure 44:
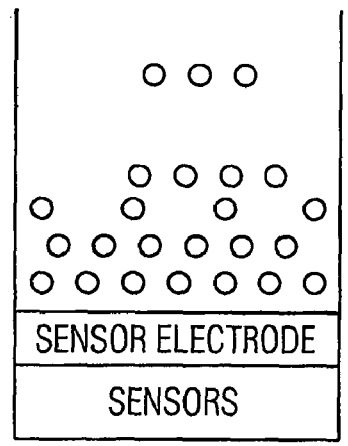
FIG. 44 shows a diagram of an MAIA sensor provided with a surface suspension colloidal interface.

FIG. 43 shows a diagram of MAIA sensor 100 with a bio-functionalized binding surface. The sensor 100 has a sensor electrode 101. Antibodies 103 are linked to the sensor electrode 101 by linkers 102. A sample is introduced to the sensor 100. If antigens 105 corresponding to the antibodies 103 linked to the sensor 100 are present in the sample, then they become bound to the sensor 100. Antigens bound to the sensor may be detected by changes to one or more resonant features of the sensor 100, as described above. Moreover, particular antigens may be identified by characteristic changes to the resonant features. This example illustrates the use of an MAIA sensor as a biosensor.

Example 5

In Vitro Gas Detection

Figure 45:
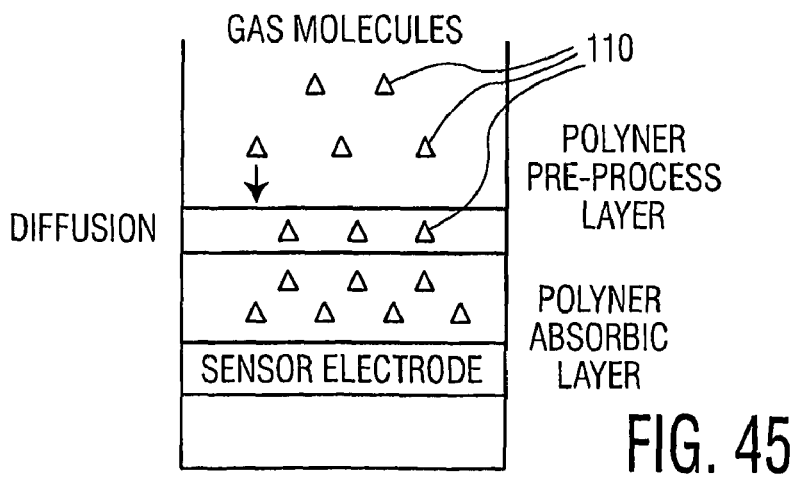
FIG. 45 shows a diagram of gas molecules interacting at a surface of an MAIA sensor

FIG. 45 shows a diagram of gas molecules 110 interacting at a surface. The diagram illustrates the diffusion of molecules 110 at a polymer pre-processing layer 112 and a polymer-absorbing layer 114. A MAIA sensor 10 can be used to detect the presence of the gas molecules 110 and to track the chemical process.

Example 6

Generalized Signal Detection

Figure 46:
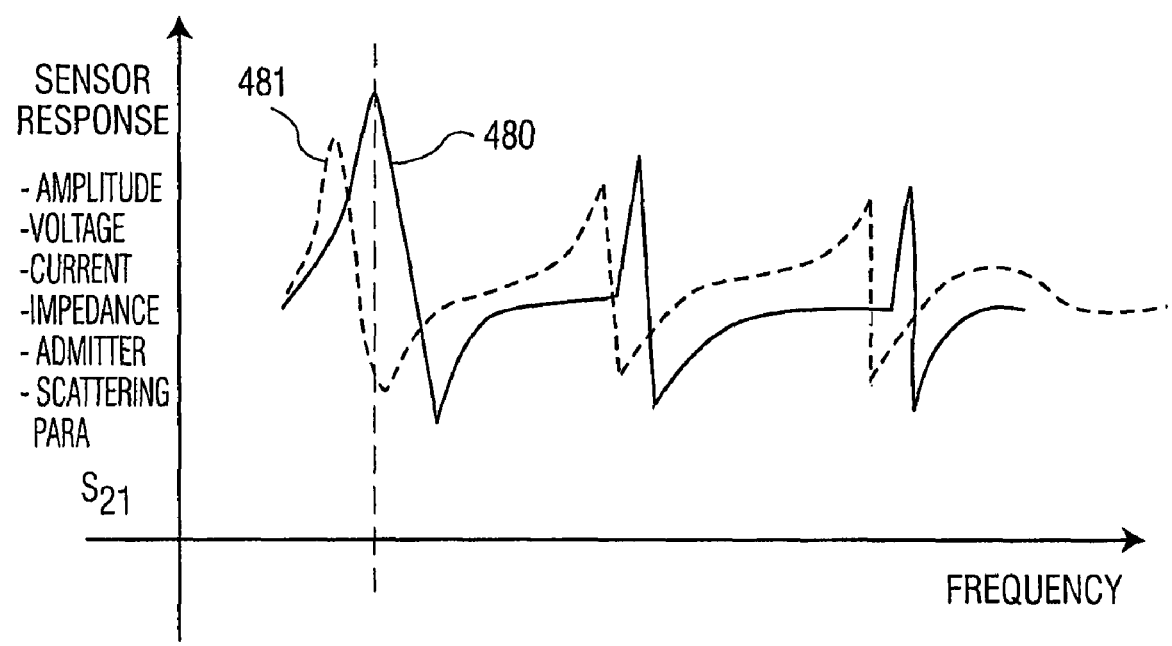
FIG. 46 shows an example of a comparison of a measured signal with a reference signal wherein the measured signal is offset from the reference signal indicating an anomaly in the interfacial area.

FIG. 46 shows an example of how the signal detection operation works, according to an exemplary embodiment of the invention. A signal parameter of the sensor can be used in order to determine various features and aspects of what is occurring at a certain layer that is being interrogated. The signal response or resonance feature can be, for example, frequency, amplitude, voltage, current, impedance, admittance, scattering, transmission parameters or combinations of these responses. A signal 480 is the base signal that the sensor emits during normal operation. The signal 481 is the signal that the sensor emits that indicates the occurrence of an event. The change between the signal 480 and the signal 481 is used to create a signature that can be used for future reference in determining the importance of events.

In yet another exemplary embodiment, an MAIA sensor may be excited at two or more frequencies simultaneously.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A sensor system comprising:
 a sensor; and
 an actuator for actuating said sensor; said actuator being enabled for operation at a first operating condition of said sensor when placed proximate to a sample, and wherein said actuator is enabled for a second operating condition of the sensor when placed proximate to the sample.

2. The sensor system of claim 1, wherein said actuator is enabled for operation at a plurality of frequencies at which said sensor is actuated.

3. The sensor system of claim 1, wherein said actuator is enabled for operation at a plurality of amplitude at which said sensor is actuated.

4. The sensor system of claim 1, wherein said actuator is enabled for operation at a plurality of phases at which said sensor is actuated.

5. The sensor system of claim 1, wherein the sensor is an acoustic sensor comprising a piezoelectric material.

6. The sensor system of claim 1, further comprising a signal processor that compares a response parameter of the sensor to another instance of that response parameter.

7. The sensor system of claim 1, further comprising a signal processor that compares a response parameter of the sensor to a reference signature response.

8. The sensor system of claim 1, further comprising a functionalized interfacial surface.

9. The sensor system of claim 8, wherein the interfacial surface is functionalized with antibodies attached to the sensor surface.

10. The sensor system of claim 8, wherein the interfacial surface is functionalized with cells attached to the sensor surface.

11. The sensor system of claim 1, wherein said actuator is enabled for exciting the sensor at two or more frequencies, simultaneously.

12. The sensor system of claim 1, wherein said actuator is enabled for excitation at a fundamental resonant frequency and at least one higher harmonic of said fundamental resonant frequency.

13. The sensor system of claim 1 having a plurality of sensors.

14. The sensor system of claim 13, wherein a plurality of actuators are enabled for exciting said plurality of sensors.

15. A sensor system, comprising:
a sensor;
an actuator for actuating said sensor to cause an acoustic response at said sensor, said actuator configured for variation of an operating condition of the sensor when the sensor is placed proximate to a sample; and
a signal processor for capturing the acoustic response.

16. The sensor system of claim 15, wherein the signal processor captures one or more response parameters of said acoustic response.

17. The sensor system of claim 16, wherein the signal processor captures the response frequency of said acoustic response.

18. The sensor system of claim 16, wherein the signal processor captures the response amplitude of said acoustic response.

19. The sensor system of claim 16, wherein the signal processor captures the response phase of said acoustic response.

20. The sensor system of claim 16, wherein the signal processor captures the response Q-factor of said acoustic response.

21. The sensor system of claim 16, wherein the signal processor captures the response impedance of said acoustic response.

22. The sensor system of claim 15, wherein the signal processor captures two or more response parameters of said acoustic response.

23. The sensor system of claim 15, wherein the signal processor compares a response parameter of the sensor to another instance of that response parameter.

24. The sensor system of claim 15, wherein the signal processor compares a response parameter of the sensor to a reference signature response to characterize a biological process.

25. The sensor system of claim 15, wherein said sensor is configured to have a fundamental frequency selected to match the resonant frequency of a target particle.

26. The sensor system of claim 15, wherein the actuator is configured to actuate the sensor at an amplitude selected to nondestructively interrogate the sensor interface.

27. The sensor system of claim 15, wherein the actuator is configured to actuate the sensor at an amplitude selected to destructively interrogate the sensor interface.

28. The sensor system of claim 15, further comprising a preprocessor for selectively introducing a sample to said sensor.

29. The sensor system of claim 28, wherein the preprocessor comprises a selective membrane.

30. The sensor system of claim 28, wherein the preprocessor comprises an acoustic field.

31. The sensor system of claim 28, wherein the preprocessor comprises a magnetic field.

32. The sensor system of claim 28, wherein the preprocessor comprises an electric field.

33. The sensor system of claim 28, wherein the preprocessor comprises an optical field.

34. The sensor system of claim 28, wherein the preprocessor comprises a thermal gradient.

35. A method for sensing comprising the steps of:
providing a sensor proximate a sample to be sensed;
exciting the sensor at a first operating condition;
measuring a resonance feature of said sensor;
changing the operating condition of said sensor to at least one additional operating condition, and
measuring the resonance feature of said sensor at said at least one additional operating condition.

36. The method of claim 35, wherein the resonance feature is resonant frequency.

37. The method of claim 35, wherein the resonance feature is amplitude.

38. The method of claim 35, wherein the resonance feature is phase.

39. The method of claim 35, wherein the resonance feature is Q-factor.

40. The method of claim 35, wherein the first operating condition is the fundamental frequency of the sensor and sample system, and the at least one additional operating condition is a higher order harmonic of the fundamental frequency of the sensor and sample system.

41. The method of claim 35, further comprising the steps of measuring a second resonance feature at the first operating condition and measuring the second resonance feature at the at least one additional operating condition.

42. The method of claim 35, further comprising the step of:
comparing the resonance feature measurements to resonance feature measurements taken at a different time at the same operating condition.

43. The method of claim 35, further comprising the step of:
comparing the resonance feature measurements to a reference signature.

44. A method for sensing comprising the steps of:
selecting an interrogation distance from a surface of an excitable sensor,
exciting the sensor at a frequency that interrogates at the selected interrogation
distance from said surface of said sensor, and
measuring a resonance feature of said sensor.

45. The method of claim 44, wherein the resonance feature is resonant frequency.

46. The method of claim 44, wherein the resonance feature is amplitude.

47. The method of claim 44, wherein the resonance feature is phase.

48. The method of claim 44, wherein the resonance feature is Q-factor.

49. The method of claim 44, further comprising the step of measuring a second resonance feature of said sensor.

50. A method for sensing comprising the steps of;
providing a sensor with known mass and fundamental frequency proximate a sample containing a particle to be sensed;
exciting the sensor at a fundamental frequency of the sensor coupled to the particle;
measuring the resonant frequency of said coupled sensor and particle; calculating the diameter of the particle coupled to the sensor using the measured resonant frequency.

* * * * *